United States Patent [19]

Chen

[11] Patent Number: 5,571,680
[45] Date of Patent: Nov. 5, 1996

[54] HOMOGENEOUS IMMUNOASSAYS AND ENZYME BASED ASSAYS OF ANALYTES USING CAPILLARY ELECTROPHORESIS

[75] Inventor: Fu-Tai A. Chen, Brea, Calif.

[73] Assignee: Beckman Instruments, Inc., Fullerton, Calif.

[21] Appl. No.: 184,791

[22] Filed: Jan. 21, 1994

[51] Int. Cl.$^6$ ................................................. G01N 33/573
[52] U.S. Cl. ........................ 435/7.4; 204/452; 435/4; 435/7.1; 436/512; 436/516; 436/800
[58] Field of Search ........................... 204/180.1; 435/4, 435/7.4, 7.1, 18, 23, 24, 512; 436/516, 800

[56] References Cited

U.S. PATENT DOCUMENTS

| | | | |
|---|---|---|---|
| 5,137,609 | 8/1992 | Manian et al. | 204/180.1 |
| 5,145,567 | 9/1992 | Hsieh et al. | 204/180.1 |

OTHER PUBLICATIONS

Zhao et al., "Detection of 100 molecules of product formed in a fucosyltransferase reaction", *Glycobiology*, vol. 4, No. 2, pp. 239–242, (1994).

Chen et al., "Characterization of proteins by capillary electrophoresis in fused–silica columns: Review on serum protein analysis and application to immunoassays", *Eeletrophoresis*, vol. 15, pp. 13–21, (1994).

Chen et al., "Feasibility Studies for Simultaneous Immunochemical Multianalyte Drug Assay by Capillary Electrophoresis with Laser–Induced Fluorescence", *Clinical Chemistry*, vol. 40, No. 9, pp. 1819–1822, (1994).

Shimura et al., "Affinity Probe Capillary Electrophoresis: Analysis of Recombinant Human Growth Hormone with a Fluorescent Labeled Antibody Fragment", *Analytical Chemistry*, vol. 66, pp. 9–15, (1994).

Lee et al., "Capillary zone electrophoresis for the quantitation of oligosaccharides formed through the action of chitinase", *Electrophoresis*, vol. 12, pp. 636–640, (1991).

Nielsen et al., "Separation of antibody–antigen complexes by capillary zone electrophoresis, isoelectric focusing and high–performance side–exclusion chromatography", *Journal of Chromatography*, vol. 539, pp. 177–185, (1991).

Zhao et al., "Low–cost laser–induced Fluorescence detector for micellar capillary zone electrophoresis, Detection at the zeptomol level of tetramethylrhodamine thiocarbamyl amino acid derivatives", *Journal of Chromatography*, vol. 608, pp. 117–120, (1992).

Dovichi et al., "The One Hundred Molecule Problem: High Sensitivity Fluorescence Assay of Biological Systems", *Abstracts of Papers of the American Chemical Society*, 206th ACS National Meeting, Aug. 22–27, 1993, Abstract 93.

Southwick et al., "Cyanine Dye Labeling Reagents–Carboxymethylindocyanine Succinimidyl Esters", *Cytometry*, vol. 11, pp. 418–430, (1990).

S. D. Lidofsky, T. Imasaka & R. N. Zare: "Laser Fluorescence Immunoassay of Insulin"; Analytical Chemistry, vol. 51, No. 11, Sep. 1979, pp. 1602–1605.

N. Ichinose, G. Schwedt, F. Schnepel & K. Adachi; "Biomedical and Clinical Chemistry"; Fluorometric Analysis in Biomedical Chemistry; Chemical Analysis, pp. 125 & 126.

Fluorolink–AB™ Cy3™ Labeling Kit Cat. No. A33000. Oct. 1993.

*Primary Examiner*—Lila Feisee
*Assistant Examiner*—Susan C. Wolski
*Attorney, Agent, or Firm*—William H. May; Janis C. Henry

[57] ABSTRACT

Homogeneous immunoassays and enzyme-substrate assays which use capillary electrophoresis and fluoescent detection systems are described. The method is useful for detecting and/or quantitating the concentration of analytes in a sample.

12 Claims, 19 Drawing Sheets

CPG-3'-AMINE-(FMOC)+1) 10 CYCLES OF
d(T) + 2) N-MMT-C₆-AMINO MODIFIER
↓ H⁺
CPG-3'-AMINE-(FMOC)-d(T)₁₀-5'-C₆ AMINE
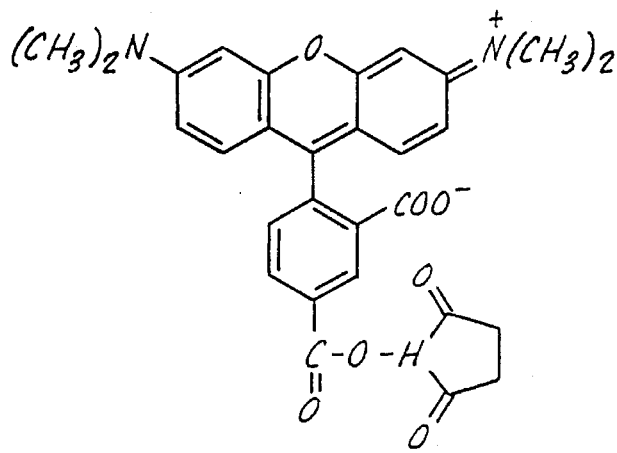
AMMONIA
↓
3'-AMINE-d(T)₁₀-5'-C₆-NH-TMR
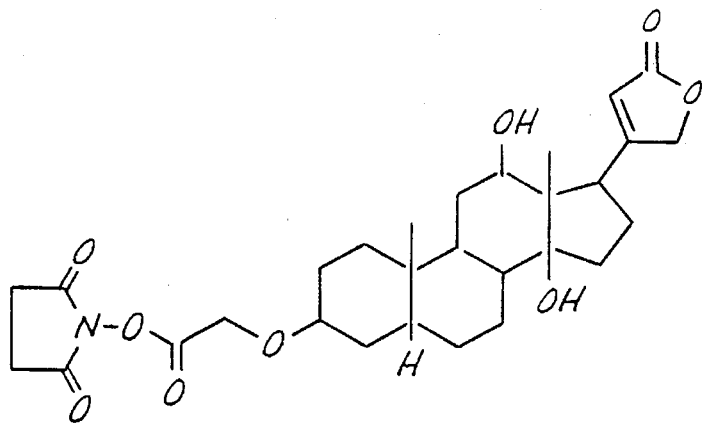
↓
DIGOXIGENIN-NH-3'-d(T)₁₀-5'-C₆-NH-TETRAMETHYLRHODAMINE
_FIG. 15._

HOMOGENEOUS IMMUNOASSAYS AND ENZYME BASED ASSAYS OF ANALYTES USING CAPILLARY ELECTROPHORESIS

FIELD OF THE INVENTION

The invention relates to highly sensitive and rapid homogeneous immunoassays and enzyme substrate assays. More specifically, the present invention relates to homogeneous assays which employ capillary electrophoresis in concert with detectably labeled immunochemicals to permit the detection and/or quantification of minute concentrations of a target analyte. The present invention relates to both the methods of conducting the assays and to the reagents employed therein.

BACKGROUND OF THE INVENTION

The ability to detect and/or quantitate the concentration of a pharmacological agent, metabolite, or toxin is a central aspect of the modem diagnosis and management of disease.

In some cases, such analytes can be detected directly, by assaying their biological activities. In most cases, however, it is more efficient to detect such molecules by virtue of their capacity to specifically bind to antibodies, or by their physical characteristics (such as electrophoretic mobility).

Immunoassays are assay systems that exploit the ability of an antibody to specifically recognize and bind to a particular target analyte. The concept of immunoassays is based on a specific chemical reaction between an antibody and its corresponding antigen. Quantitation involves the separation of antibody bound antigen from the free antigen followed by detection of antibody bound antigen or free antigen in solution depending upon the specific analytical scheme. Such assays are used extensively in modem diagnostics (See, Fackrell, *J. Clin. Immunoassay* 8:213–219 (1985); Yolken, R. H., *Rev. Infect. Dis.* 4:35 (1982); Collins, W. P., In: *Alternative Immunoassays*, John Wiley & Sons, New York (1985); Ngo, T. T. et al., In: *Enzyme Mediated Immunoassay*, Plenum Press, New York (1985)).

There are many variations of immunoassay and the critical steps are either physical separation or discrimination and detection. Immunoassays that require physical separation are termed heterogeneous immunoassays. In contrast, homogeneous immunoassays are designed such that the removal of bound from unbound species is unnecessary. Because homogeneous assays lack a separation step, and are more easily automated, they are more desirable than heterogeneous assays in applications that entail the screening of large numbers of patients.

Analytes present at concentration levels below $10^{-9}M$ are generally assayed using a solid-phase based "sandwich" or competitive method. Typically, in such assays, the antigen of interest competes with a labeled antigen for a judicious amount of antibody. A direct immunoassay is typically a sandwich assay involving two antibodies binding to different antigenic sites of an antigen. One antibody is bound to a solid phase material, and is employed to harvest the antigen. The other antibody is labeled and used to generate quantitative information from the bound antigen (Cone, E. J. et al., *J. Forens. Sci.* 35:786–781 (1990); Baugh, L. D. et al., *J. Forens. Sci.* 36:79–85 (1991); Standefer, J. C. et al., *Clin. Chem.* 37:733–738 (1991)).

In order to facilitate the detection of antibody binding, one or more reaction analytes is typically labeled (as with a radioisotope, an enzyme, a fluorescent moiety, a chemiluminescent moiety, or a macroscopic label, such as a bead, etc.) (see, Chard, T. et al., In: *Laboratory Techniques and Biochemistry in Molecular Biology* (Work, T. S., Ed.), North Holland Publishing Company, New York (1978); Kemeny, D. M. et al. (Eds.), *ELISA and Other Solid Phase Immunoassays*, John Wiley & Sons, New York (1988)). Radioisotopes have long been used in immunoassays. O'Leary, T. D. et al., for example describe a radioimmunoassay for digoxin serum concentrations (O'Leary, T. D. et al., *Clin. Chem.* 25:332–334 (1979)). The difficulty of handling such hazardous materials, and the problem of radioactive decay have led to the development of immunoassays that use other labels.

Enzymes, in particular, are now widely used as labels in immunoassay formats. The enzyme-multiplied immunoassay technique (EMIT®, Syva Co.) has been used to assay acetaminophen, cocaine and other analytes (Helper, B. et al., *Amer. J. Clin. Pathol.* 81:602–610 (1984); Cambell, R. S. et al., *J. Clin. Chem. Clin. Biochem.* 24:155–159 (1986); Khanna, P., U.S. Pat. No. 5,103,021; Cone, E. J. et al., *J. Forens. Sci.* 35:786–781 (1990); Baugh, L. D. et al., *J. Forens. Sci.* 36:79–85 (1991); Standefer, J. C. et al., *Clin. Chem.* 37:733–738 (1991); Roberts, D. W. et al., *J. Pharmacol. Exper. Therap.* 241:527–533 (1987); Bartolone, J. B. et al., *Biochem. Pharamcol.* 37:4763–4774 (1988))

In addition to enzymes, fluorescent moieties are frequently used as labels (see, Ichinose, N. et al., In: *Fluorometric Analysis in Biomedical Chemistry*, Vol 110, Chemical Analysis (Winefordner, J. D. et al., Eds.) John Wiley & Sons, New York (1991)). For example, a fluorescence polarization immunoassay format for cocaine has been described (TDx®, Abbott Laboratories, Inc.), and has been found to be approximately equivalent to the EMIT® formats (Schwartz, J. G. et al., *Amer. J. Emerg. Med.* 9:166–170 (1991)). The TDx® format has also been used to assay acetaminophen serum levels (Koizumi, F. et al., *Tohoku J. Exper. Med.* 155:159–(1988); Edinboro, L. E. et al., *Clin. Toxicol.* 29:241-(1991); Okurodudu, A. O. et al., *Clin. Chem.* 38:1040 (1992)), and serum digoxin levels (Okurodudu, A. O. et al., *Clin. Chem.* 38:1040 (1992)). Wong, S. H. Y. et al., have described the use of an automated (OPUS) analyzer to measure digoxin concentration in a monoclonal antibody mediated, fluorescence-based assay protocol (Wong, S. H. Y. et al., *Clin. Chem.* 38:996 (1992)). Lee, D. H. et al. also disclose the use of a fluorescence polarization assay and a chemiluminescent assay format to assay digoxin levels (Lee, D. H. et al., *Clin. Chem.* 36:1121 (1990)).

As indicated, electrophoretic methods have also been used to facilitate the detection of target analytes. Such methods exploit the fact that molecules in solution have an intrinsic electrical charge. Thus, in the presence of an electric field, each molecular species migrates with a characteristic "electrophoretic" mobility thereby causing the various species present to separate from one another. Under the influence of such a field, all of the variants will move toward a designated charge opposite to the charge of the variants; those having a lower electrophoretic mobility will move slower than, and hence be separated from, those having a (relative) higher electrophoretic mobility.

Immunological electrophoretic methods, such as Immunofixation electrophoresis ("IFE"), Immunoelectrophoresis ("IEP"), and immunosubtraction electrophoresis ("ISE") have been described which combine the capacity of electrophoretic methods to separate molecular species with the detection capacity of immunoassays. Such assays have been used to detect and quantitate serum proteins.

IEP and IFE are related procedures (Beckman Bulletin EP-2. "Immunoelectrophoresis Applications Guide."

(1991)). IFE is a two stage procedure using agarose gel protein electrophoresis in the first stage and immunoprecipitation in the second. In a clinical setting for the analysis of immunoglobulins, a clinical sample (e.g., whole blood, serum, plasma, urine, cerebrospinal fluid) is placed in multiple positions ("lanes") on an agarose gel. When an electric field is applied to the gel-containing sample, the immunoglobulins will traverse the gel from anionic to cationic electrode. Thereafter, antisera comprising antibodies to specific immunoglobulin classes (typically IgG, IgA, IgM, kappa and lambda) are applied to specific lanes. The gel and antisera are incubated, during which time immune complexes form between the specific immunoglobulins and the antibodies. The location of such immune complexes are visualized by staining. By using a reference pattern on the gel, one can then determine the type of immunoglobulin present on the gel. The presence of a particular band is thus indicative of the presence of an M-protein corresponding to a particular immunoglobulin type. Methods of conducting IFE are disclosed by Chen, F-. T. A., U.S. Pat. No. 5,202,006; Chen, F-. T. A., U.S. Pat. No. 5,120,413; Hsieh, Y-. Z. et al., U.S. Pat. No. 5,145,567; all herein incorporated by reference).

The PARAGON® electrophoresis system (Beckman Instruments, Inc., Fullerton, Calif., U.S.A.) is a commercially available system for conducting both IFE and IEP (See also, Gebott et al., U.S. Pat. No. 4,669,363; Pentoney, S. L., U.S. Pat. No. 5,208,466, herein, herein incorporated by reference; Beckman Bulletin EP-3 "Paragon® Serum Protein Electrophoresis II (SPE-II) Applications Guide" (1990); Beckman Bulletin EP-2. "Immunoelectrophoresis Applications Guide" (1991); Beckman Bulletin EP-4 "Immunofixation Electrophoresis Applications Guide" (1991); Beckman Instructions 015-246513-H "Paragon® Electrophoresis System-IFE" (1990); Beckman Bulletin EP-6 "High Resolution Electrophoresis in the Detection of Monoclonal Gammopathies and Other Serum Protein Disorders." (1990); Chen, F-. T. A. et al. Clin. Chem. 37:14–19 (1991)).

Immunosubtraction electrophoresis (ISE) is a variation of IFE (Aguzzi, F. et al., Estratto dal. Boll. 1st Sieroter, Milanese 56:212–216 (1977); White, W. A. et al., Biochem. Clin. 10:571–574 (1986); Merlini, G. et al., J. Clin. Chem. Biochem. 21:841–844 (1983); Liu, C-. M. et al., U.S. Pat. No. 5,228,960, herein incorporated by reference). In ISE, however, the sample is pretreated with an insolubilized antibody directed to a particular "target" protein. If the target protein is present, it will bind to the antibody and thus be removed from the sample. The sample is then applied to a gel and subjected to electrophoresis. If the target protein had been present in the initial sample, visualization of the proteins in the gel would reveal a negative band (i.e. an absence of staining) at the position in the gel where the removed band would have migrated to, had it not been removed by the antibody. Thus, the absence of a particular band is indicative of the presence of the corresponding target protein in the sample.

IEP, IFE and ISE each require multiple steps, and the preparation and use of a separation gel and a signal-generating stain. The labor intensive nature of these procedure is an obvious impediment in a clinical setting. Additionally, the amount of disposable end-products associated with these procedures can further increase the allied costs associated with these procedures.

In view of the deficiencies of these methods in clinical settings, less labor-intensive methods that permit greater throughput with lower cost have been sought. One such method is "Capillary Electrophoresis" ("CE") (Chen, F-. T. A. et al., Clin. Chem. 77:14–19 (1991); Nielsen et al., J. Chromatogr. 539:177 (1991); U.S. Pat. No. 5,120,413, all herein incorporated by reference). Capillary electrophoresis (CE) is one of the most powerful tools yet developed for the separation of ionic species such as proteins, peptides and other water soluble molecules.

The method permits rapid and efficient separations of proteins (such as human growth hormone) (Grossman, P. et al., Anal. Chem. 61:1186–1194 (1989)), and other charged substances. Separation of the constituents of clinical samples can typically be accomplished in less than 20 minutes. Separation of proteins in plasma and serum sample have been attempted by Jorgenson, J. W. et al. (Science 222:266–272 (1983)) and Hjerten, S. (Electrophoresis 11:665–690 (1990)). The feasibility of routine analysis of serum proteins by CE in an untreated fused-silica capillary has been demonstrated (Chen, F-. T. A. et al., Clin. Chem. 37:14–19 (1991); Gordon, M. G. et al., Anal. Chem. 63:69–72 (1991)).

In general, CE involves introducing a sample into a capillary tube, i.e. a tube having an internal diameter of from about 2 μm to about 2000 μm (preferably, less than about 50 μm, most preferably, about 25 μm or less) and applying an electric field to the tube (Chen, F-. T. A., J. Chromatogr. 516:69–78 (1991); Chen, F-. T. A. et al., J. Chromatogr. 15:1143–1161 (1992)). Since each of the sample constituents has its own individual electrophoretic mobility, those having greater mobility travel through the capillary tube faster than those with slower mobility. Hence, the constituents of the sample are resolved into discrete zones in the capillary tube during their migration through the tube. (Heegard, N. H. H. et al., Anal. Chem. 64:2479–2482 (1992); Gordon, M. J. et al., Anal. Chem. 63:69–72 (1991); F-. T. A., U.S. Pat. No. 5,202,006; Chen, F-. T. A., U.S. Pat. No. 5,120,413; Hsieh, Y-. Z. et at., U.S. Pat. No. 5,145,567). The method is well-suited to automation, since it provides convenient on-line injection, detection and real-time data analysis. Detection of protein in CE is usually based on the intrinsic ultraviolet (UV) absorbance of the peptide bond at or near 200 nm, which provides a detection limit of about $10^{-5}$M. Fluorescence-based detection assays have, however, also been described (Lee, T. T. et al., J. Chromatogr. 595:319–325 (1992)).

The capillary column used in CE must be capable of withstanding a wide range of applied electrophoretic fields of between about 10 v/cm to about 1000 v/cm. Fused silica is a preferred material for the capillary tube because it can withstand such voltages, and because the inner walls ionize to create the negative charge which causes the desired electroosmatic flow.

In some cases, however, the use of fused silica can have undesired effects. Proteins, for example, are polyelectrolytes, consisting of both positively and negatively charged moieties. The pKa of the guanidinium and e-$NH_2$ groups of the arginine and lysine residues, respectively, is 12.0 and 10.5, and these groups comprise most of the positively charged moieties in proteins, other than the a-NH2 terminal (which has a pKa of between 7.5 and 9) and histidine residues. Because a fused-silica surface contains weakly acidic silanol groups that act as cation-exchangers, the protein-silica surface interaction can be viewed as an ion-exchange phenomenon (Lauer, H. H. et al., Anal. Chem. 58:166–169 (1986); Green, J. S. et al., J. Chromatogr. 478:63–70 (1989)). Early efforts to electrophorese proteins in untreated fused-silica capillaries resulted in broad peaks and irreproducible migration of the sample zones (Jorgenson, J. W. et al., Science 222:266–272 (1983)). The interaction of proteins with the silica wall is believed to be responsible for degrading the efficiency of protein separations by CE in untreated fused-silica capillaries.

Capillaries that have been coated with a material such as alumina, beryllium, Teflon®, glass, quartz, etc. or combinations thereof, have been found to limit protein absorption to the untreated walls during the electrophoretic separation procedure. Such coated capillaries have enjoyed widespread use. However, eventually these coatings break down in an unpredictable manner. Thus, the use of uncoated capillaries has been generally preferred.

To avoid or minimize the protein-silica interaction, protein separations by CE in untreated fused-silica capillaries have previously been performed in buffers having a pH either substantially higher than the isoelectric points of the sample proteins (Lauer, H. H. et al., *Anal. Chem.* 58:166–169 (1986)), or $\leq 2.5$ (McCormick, R., *Anal. Chem.* 60:2322–2327 (1988)), or in a relatively basic buffer with a high salt concentration (Greene, J. S. et al., *J. Chromatogr.* 478:63–70 (1989)). Greene, J. S. et al. (*J. Chromatogr.* 478:63–70 (1989)) demonstrated the high efficiency of separation of model proteins by CE in untreated fused-silica column using 0.1M CHES (CHES: 2-(Cyclohexylamino)ethanesulfonic acid) buffer in 0.25M potassium sulfate at pH 9.0. However, using a similar zwitterionic buffer system such as BES (BES: N,N-Bis(2-hydroxyethyl)-2-aminoethanesulfonic acid) and HEPES (HEPES: 4-(2-Hydroxyethyl)piperazine-1-ethanesulfonic acid;) at pH 7.0 and 8.0, respectively, in 0.25M potassium sulfate, model proteins are poorly resolved. As the pH of the buffer decreases from 9.0 to 7.0, proteins become more positively charged, thus increasing the protein-silica wall interaction. To avoid this increased interaction, the amount of potassium sulfate has to be increased, resulting in a higher conductivity in CE. Furthermore, proteins in complex mixtures, such as serum, ascites fluid and tissue extracts, are relatively difficult to separate, due to the presence of lipids and their associated proteins.

In view of the importance of accurately detecting and quantitating analyte, and especially protein, concentrations in samples, it would be particularly desirable to possess a generally applicable methods would allow for separation of model proteins and complex protein mixtures. A capillary electrophoresis technique that could additionally be employed to resolve organic analytes (such as pollutants, toxins, etc.) and which could provide a facile means of detection would also be highly desirable. The present invention provides such methods.

SUMMARY OF THE INVENTION

The present invention provides highly sensitive and rapid homogeneous immunoassay and enzyme-substrate assays which employ capillary electrophoresis in concert with detectably labeled immunochemicals or enzyme substrates to permit the detection and/or quantification of minute concentrations of a target analyte.

In detail, the invention provides methods for assaying the concentration of an analyte in a sample which comprises the steps:

(A) incubating the sample in the presence of an excess of an immunoglobulin, the immunoglobulin containing a fluorophore and being capable of specifically binding to the analyte, wherein the incubation is conducted under conditions sufficient to permit the immunoglobulin and the analyte to form an immunoglobulin-analyte complex;

(B) subjecting an amount of incubated sample of step (A) to capillary electrophoresis, the capillary electrophoresis being conducted under conditions sufficient to separate the immunoglobulin-analyte complex from uncomplexed immunoglobulin; and (C) assaying the concentration of analyte by detecting the immunoglobulin-analyte complex; the detection being accomplished by inducing fluorescence of the fluorophore, and detecting the induced fluorescence; the detected induced fluorescence being directly proportional to the concentration of the analyte in the sample.

Exemplary embodiments also include enzyme-substrate reactions in which a sample containing an enzyme is allowed to specifically bind to a labeled protein and reaction products of the enzyme-substrate reaction are analyzed by CE. Such methods include the steps of:

(A) incubating the sample in the presence of an enzyme substrate, the enzyme substrate containing a fluorophore and being capable of specifically binding to the enzyme, wherein the incubation is conducted under conditions sufficient to permit the enzyme substrate and the enzyme to form an enzyme substrate-enzyme complex and react to form reaction products;

(B) subjecting an amount of incubated sample of step (A) to capillary electrophoresis, the capillary electrophoresis being conducted under conditions sufficient to separate the reaction products from labeled enzyme substrate; and (C) detecting the reaction products; the detection being accomplished by inducing fluorescence of the fluorophore, and detecting the induced fluorescence, the detected induced fluorescence being directly proportional to the concentration of reaction product in the sample.

In accordance with the present invention, immunoglobulin containing fluorophores and enzyme substrate containing fluorophores are immunoglobulins and enzyme substrates labeled with a fluorophore during a labeling reaction.

The invention is also particularly concerned with the use of fluorophores selected from the group consisting of fluorescein, isothiocyanate, rhodamine, phycoerythrin, phycocyanin, allophycocyanin, o-phthaldehyde label, fluorescamine, tetramethylrhodamine and BODIPY® labeled oligonucleotide (4,4-difluoro-4-bora-3a-diaza-s-indacene, Molecular Probes, Inc., Eugene, Oreg.

The invention also concerns a method of assaying the concentration of an analyte in a sample which comprises the steps:

(A) incubating the sample in the presence of an immunoglobulin, the immunoglobulin being capable of specifically and competitively binding to the analyte and to a fluorophore, wherein the incubation is conducted under conditions sufficient to permit the immunoglobulin and the analyte, or the immunoglobulin and the fluorophore to form an immunoglobulin-analyte complex;

(B) subjecting an amount of any immunoglobulin-analyte or immunoglobulin-fluorophore complex of step (A) to capillary electrophoresis, the capillary electrophoresis being conducted under conditions sufficient to separate the complexes from uncomplexed fluorophore; and (C) assaying the concentration of analyte by detecting the immunoglobulin-fluorophore complex; the detection being accomplished by inducing fluorescence of the fluorophore, and detecting the induced fluorescence; the detected induced fluorescence being inversely proportional to the concentration of the analyte in the sample.

The invention particularly concerns the embodiment of the above method, wherein in step (A), the fluorophore is an analyte derivative, and especially one that contains at least one nucleotidyl residue, which contains a fluorescent moiety selected from the group consisting of fluorescein, isothiocyanate, rhodamine, phycoerythrin, phycocyanin, allophycocyanin, o-phthaldehyde label, fluorescamine, tetramethylrhodamine, a BODIPY labeled oligonucleotide.

The invention particularly concerns the embodiment of the above method, wherein the analyte derivative contains an oligonucleotide (preferably a 10-mer) having at least one nucleotidyl residue which contains the fluorescent moiety The invention particularly concerns the embodiment of the above method wherein the fluorophore has the formula:

$$A\text{-}3'\text{-}[N]_x\text{-}5'\text{-}F$$

wherein A is the analyte being assayed, N is a nucleotide derivative, x is the number of nucleotidyl residues, and has a value between 1 and 20 (especially about 10), and F is a fluorescent moiety (especially tetramethylrhodamine).

The invention is particularly concerned with the use of the above methods wherein the analyte is a protein or a pharmaceutical compound, and the sample is selected from the group consisting of blood, serum, cerebrospinal fluid, urine and milk, or wherein the analyte is a non-proteinaceous organic molecule, and the sample is selected from the group consisting of water, soil, waste and foodstuff.

The invention is particularly concerned with the use immunoglobulins selected from the group consisting of a polyclonal antibody, a monoclonal antibody, an Fab fragment, an F(ab)$_2$ fragment and a single-chain immunoglobulin.

BRIEF DESCRIPTION OF THE FIGURES

In FIG. 5A, the CE was conducted using an untreated fused-silica capillary, 20 μm (i.d.)×25 cm; Applied potential, 20 kV/14 μA; Beckman protein analysis buffer. In FIG. 5B, the same sample was subjected to CE using the an SPE gel with the Paragon agarose electrophoresis system.

FIG. 6A is a capillary electropherogram of an abnormal serum protein; conditions as in FIG. 5A. FIG. 6B is an electropherogram of the same sample on SPE gel with the Paragon agarose electrophoresis system.

FIG. 7A is a capillary electropherogram; conditions as in FIG. 5A. FIG. 7B is an electropherogram of the same sample on SPE gel with the Paragon agarose electrophoresis system.

FIG. 15 shows a schematic of the synthesis of digoxigenin-3'-d(T)$_{10}$-TMR.

is that of a carboxypeptidase P digestion mixture of the mixture shown in (B).

Figure 20:
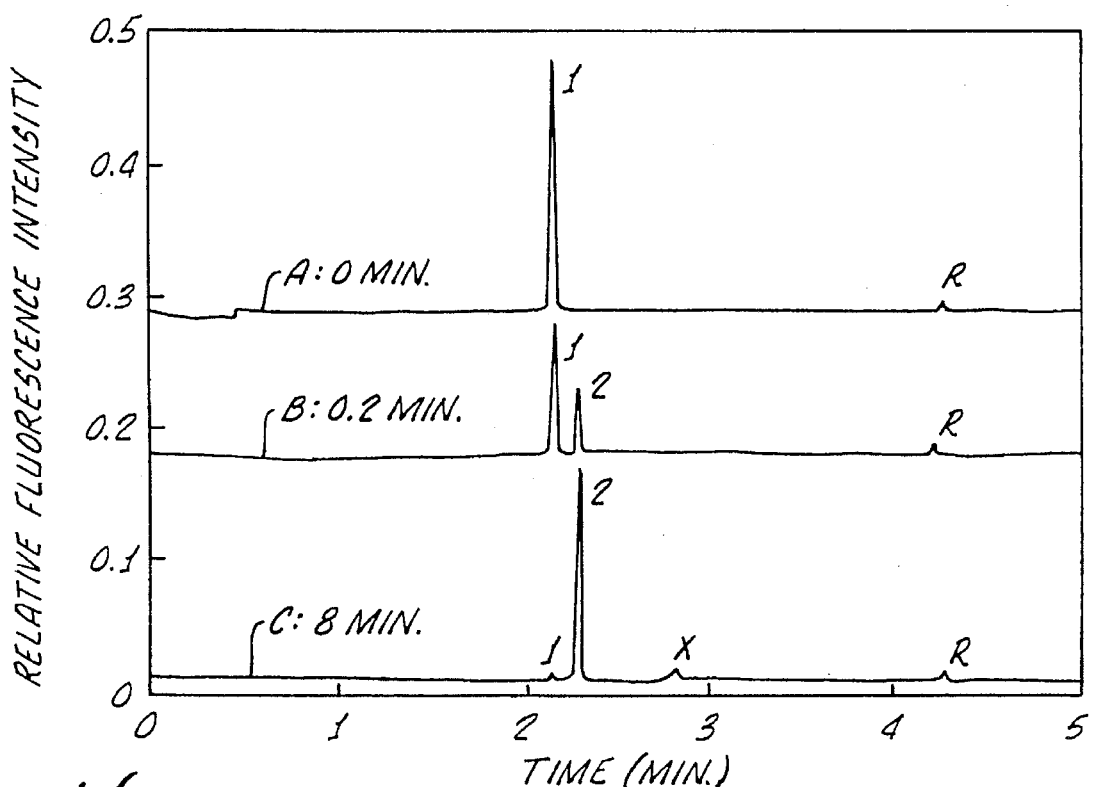

FIG. 20 shows electropherograms of a proteinase K digestion of fluoro labeled angiotensin I. Electropherogram (A) is that of the pre-digestion mixture. Electropherograms (B) and (C) are those obtained after 0.2 minutes and 8 minutes digestion, respectively.

Figure 21:
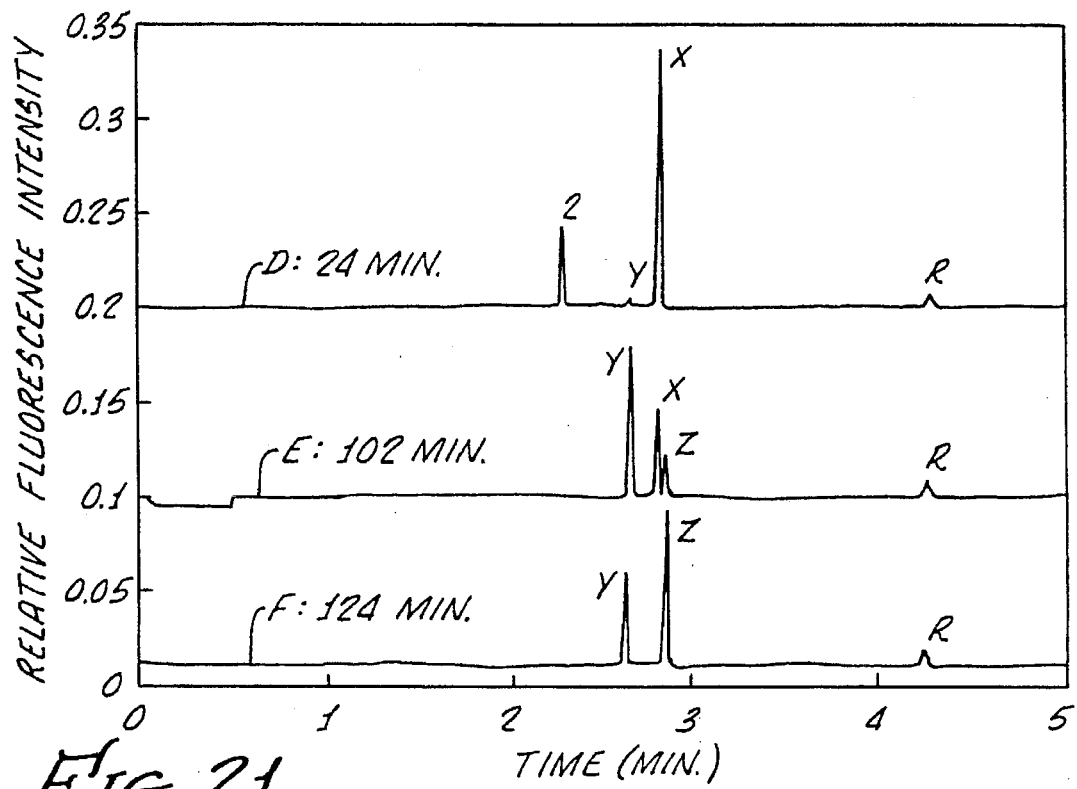

FIG. 21 shows electropherograms of a proteinase K digestion of fluoro labeled angiotensin I. Electropherogram (D) is that obtained after 24 minutes digestion. Electropherograms (E) and(F) are those obtained after 102 minutes and 124 minutes digestion, respectively.

Figure 22:
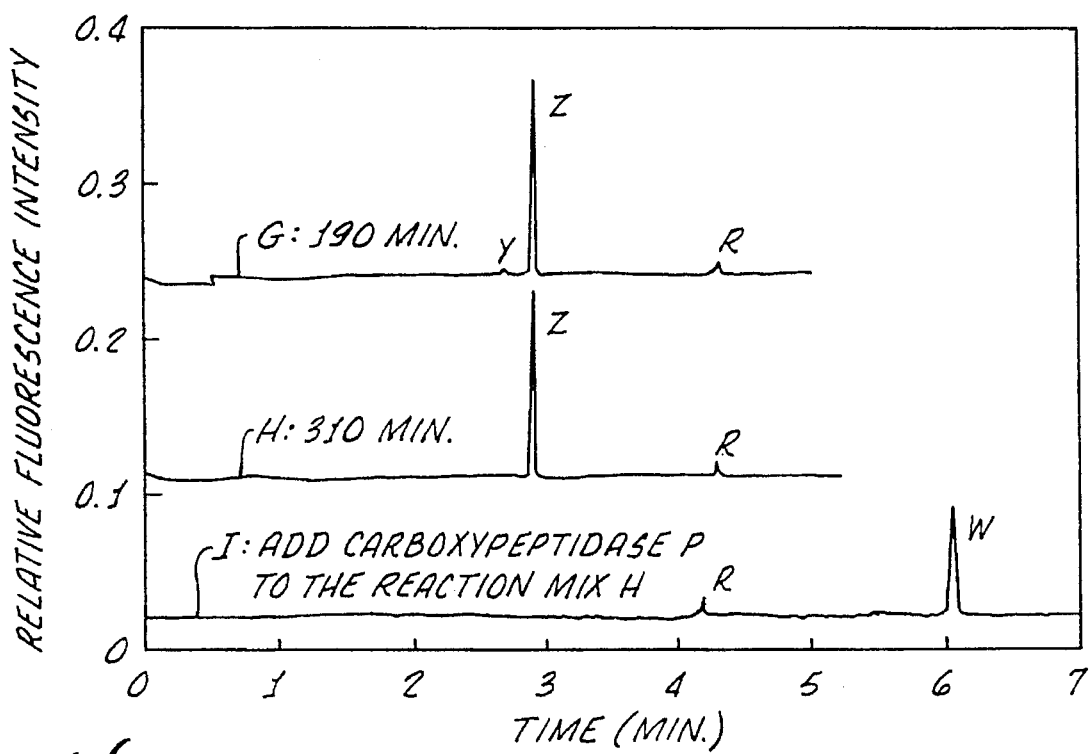

FIG. 22 shows electropherograms of a proteinase K digestion of fluoro labeled angiotensin I. Electropherograms (G) and (H) were obtained after 190 minutes and 310 minutes digestion, respectively. Electropherogram (I) was obtained after adding carboxypeptidase P to the digestion mixture shown in (H).

DESCRIPTION OF THE PREFERRED EMBODIMENTS

I. Overview of the Methods of the Present Invention

Efforts to overcome the problems incurred in using untreated capillaries and CE to analyze proteins and similar polyionic species have focused on the modification of the silica surface. Thus by using an appropriate chemical coating, or by physical masking, the zeta potential of the silica surface can be minimized or altered for specific applications. Chemical coating with a neutral functional group reduces or eliminates the interaction of silanoate (Si—O—) with the positively charged moieties of proteins. Thus, by using a silica capillary coated with polyacrylamide, it is possible to perform protein separations at neutral and acidic pH with extremely high efficiency (Hjerten, S., *J. Chromatogr.* 347:191–198 (1985)). Novotny, M. et al. (*Electrophoresis* 11:735–749 (1990)) extended the protein separation capability of Hjerten's coating to the basic pH range by introducing a stable Si—C bond for the attachment of linear polyacrylamide. Several other chemical modifications of silica surfaces have resulted in successful protein separations, but only over limited pH ranges (Novotny, M. et al., *Electrophoresis* 11:735–749 (1990); Towns, J. K. et al., *J. Chromatogr.* 516:69–78 (1990)). A pentafluoro-benzoyl coated capillary was found to be capable of mediating excellent separations of protein species having a broad range of isoelectric points (from 5 to 11 ) with a 200 mM phosphate buffer containing 100 mM KCl at a pH of 7.0. (Swedberg, S. A., *Anal. Biochem.* 185:51–56 (1990)).

Chemically-coated capillaries, however, often suffer from a gradual loss of surface coverage, particularly at high pH. Furthermore, CE with complex protein mixtures, such as milk and plasma (Jorgenson, J. W. et al., *Science* 222:266–272 (1983)), is vulnerable to protein adsorption to the coated layer, which reduces separation efficiency and reproducibility. The use of rigorous washing conditions between runs to remove the adsorbed proteins could adversely affect the capillary coating.

The present invention extends the utility of capillary electrophoresis by providing a homogeneous immunoassay format that can be performed in conjunction with untreated fused silica columns and capillary electrophoresis in order to permit the detection of very low-level analytes. Indeed, in its most preferred embodiments, the methods of the present invention permit the analysis of proteins and other analytes even when present at concentrations down to $10^{-9}$M (i.e. sub-µg/ml). Moreover, the methods of the present invention may be used to analyze proteins present in complex clinical samples. Such an accomplishment had not previously been possible. Indeed, at $10^{-1}$M of protein (for Mol. Wt. of 100 Kd, it is 10 ng/ml), the amount of protein being injected into the CE capillary is merely a few femtograms. Such a small amount of protein can easily be adsorbed in the capillary wall. The present invention provides a solution to this problem.

In addition to increased sensitivity, the methods of the present invention permit an enormous reduction in the amount of sample that must be obtained and processed. Thus, for example, a standard CE analysis can typically be conducted using less than 5 µL (depending upon the inner diameter of the column) and the sample volume requirement for each analysis is extremely small, typically in the nanoliter range or below. A realistic sample size of a few microliters of serum and assay reagents in diluted form may be sufficient. Thus, the overall reagent consumption for both the assay reaction and CE separation is at least one to two orders of magnitude less than most current immunoassays and enzyme based assays.

The methods of the present invention additionally permit CE to be used to mediate the separation of the bound from the free species in immunoassays and enzyme assays based on the above separation strategy in CE. In most practical immunoassays, either the free or the bound species must be measured in the presence of numerous potentially interfering substances. It has therefore been generally necessary to have a uniquely detectable label on one of the assay reactants. Since the species of interest will often be at a relatively low concentration, it has been necessary to use a label and detection method which would provide very good sensitivity. Furthermore, for many antigens, the antigen-antibody complex may not be readily separable from the free antibody. In those cases it has been necessary to also provide a means to enhance the separation.

In accordance with the methods of the present invention, however, it is possible to achieve effective separation of the antigen or antibody from the antigen-antibody complex by modulating the electrophoretic mobility of the antigen or antibody by chemical modification with well-defined charge-beating organic molecules (such as synthetic oligonucleotides, or other similar molecules). Oligonucleotides are a particularly preferred choice for charge modification. The phosphate groups between each pair of nucleosides each contain one negative charge at pH values above 8.0. Since the 3'- and 5'-ends of the oligonucleotide are chemically distinct, it is possible to couple an antigen molecule to one end of the oligonucleotide, and a labeled molecule for detection purposes to the other end. For use in capillary electrophoresis, fluorescent labels and laser induced fluorescence (LIF) detection (see, Ichinose, N. et al., In: *Fluorometric Analysis in Biomedical Chemistry*, Vol 110, Chemical Analysis (Winefordner, J. D. et al., Eds.) John Wiley & Sons, New York (1991); Lidofsky, S. D. et al., *Anal. Chem.* 51:1602–1605 (1979); Manian, B. S. et al., U.S. Pat. No. 5,137,609; all herein incorporated by reference) is especially preferred.

Although samples for evaluation in accordance with the methods of the present invention will be clinical samples (such as whole blood, milk, serum, plasma, urine, cerebrospinal fluid, etc.), suitable samples can include water, waste, foodstuffs, etc. Moreover, laboratory analytical samples containing enzymes for analysis in enzyme-substrate based reactions are also contemplated as being within the scope of the present invention.

Any of a wide variety of analytes may be evaluated in accordance with the methods of the present invention (e.g., proteins (such as immunoglobulins, receptors, enzymes, etc.), metabolites, substances of abuse (such as cocaine, cannabinoids, opiates, etc.), toxins, pharmacological agents, etc.). The methods of the present invention are particularly suitable for analyzing proteins, drugs and other pharmacological agents. Such analytes may be detected even if present at concentrations as low as $10^{-11}$M in the sample. Thus, a protein having a molecular weight of 100 kd, could be detected even at a concentration of 10 ng/ml. Such sensitivity is desirable since it is preferred that the samples being analyzed, especially clinical samples be diluted in an appropriate diluent prior to analysis; such dilution, facilitates inter alia achieving a desired analytical ratio, and further augments the sensitivity of the analysis. I.e., a non-diluted clinical sample, particularly serum, may contain too much assay interfering protein to permit accurate analysis. Focusing on serum, a most preferred dilution is a one part serum to ten parts of an appropriate diluent, however, dilution of up to one part serum to about 100 parts diluent can also be used. The diluent is preferably a lightly buffered saline solution, pH 7.0, such as the ICS™ diluent.

II. The Preferred CE/LIF Methods of the Present Invention

In accordance with the methods of the present invention, the detection and quantification of an analyte is accomplished using CE. The detection of the analyte is accomplished using any of a variety of immunoassay or enzyme-substrate formats.

In one preferred embodiment, a direct immunoassay is conducted. In one such assay, an antibody to a specific antigen of interest is labeled (Ab*) and permitted to complex the antigen (Ag) of interest. The immunoreaction is conducted in the presence of excess Ab* in order to assure the binding of all Ag present. The Ab*-Ag complexes thus formed are separated from free labeled Ab* by CE. The primary concern encountered in this embodiment of the invention would be the capacity of CE to resolve the Ab* from the Ab*-Ag complex. As discussed below, such resolution can be obtained in several ways. This embodiment of the invention is particularly suited for the analysis of Ag having high electrophoretic mobility. Nevertheless, the direct analysis method can be readily used to analyze concentrations of small haptens such as vitamin B-12 or digoxin. The reaction kinetics of the assay are more favorable than conventional solid phase based immunoassays or competitive immunoassays due to the presence of excess antibody in a homogeneous phase.

In another embodiment of the present invention, a direct enzyme-substrate reaction is conducted. A substrate to a specific enzyme is labelled and permitted to react with a specific enzyme in an enzyme enzyme-substrate reaction. Any labeled enzyme-substrate complex or labeled reaction product of the enzyme substrate reaction thus formed are separated from free labeled enzyme substrate by CE.

In an alternative embodiment, labeled antigen (Ag*) is provided and permitted to compete with the unlabeled antigen of the sample for binding to a limiting amount of Ab. CE is used to separate Ag* from the Ab-Ag* complex. In contrast to the direct analysis method, this embodiment is particularly suited to the analysis of Ag having low molecular weight.

Most preferably, the Ab molecules used will be monoclonal antibodies, preferably with affinity constants of $10^{-9}$ or more. In lieu of such antibody molecules, polyclonal antibodies, Fab or F(ab)$_2$ fragments, single chain antibodies, or solubilized receptors or receptor ligands can be employed.

In the preferred embodiment of using a monoclonal antibody with an affinity constant of $10^{-10}$M, an antibody concentration of 1.5 mg/ml ($10^{-5}$M) could be employed in the immunoreaction; such a concentration is capable of binding 10,000 times the level of antigen typically found in serum.

The label used in conjunction with the above embodiments may be a radioisotope, enzyme, fluorescent moiety, chemiluminescent moiety, or a paramagnetic or ferromagnetic moiety. Most preferably, however, the label will be a fluorescent moiety. Suitable fluorophores include fluorescein, isothiocyanate, rhodamine, phycoerythrin, phycocyanin, allophycocyanin, o-phthaldehyde label, fluorescamine, tetramethylrhodamine, "BODIPY" labeled oligonucleotide, or analytes bearing such fluorescent moieties, for example. Where labeling of the antibody is desired, rhodamine labels may preferably be used. Such labeled antibody may be used in direct immunoassays for protein species present at concentrations of approximately $10^{-10}$M. Any suitable method may be used to directly label the antibodies or antigens of the present invention.

Charge and mass based modifications are inevitably required for quantitative ligand analysis. The fluorescence property of labels such as β-phycoerythrin (BP*) is resistant to chemical modification. Thus, although succinylation of B-phycoerythrin results in a modified "SBP*" that migrates more slowly than BP* (depending on the extent of modification), the FQE of the succinylated form is essentially intact. These attributes can be exploited in order to produce a succinylated BP* derivative that can be readily coupled to other molecules to extend the applicability of the CE/LIF method. In addition to facilitating the labeling of antigen molecules, the use of modified fluorophores provides a means for controlling the electrophoretic mobility of the labeled molecule. The D-SBP* compound is particularly suited for use in competitive immunoassays of antigens such as folic acid, vitamin B$_{12}$, cortisols and other steroid hormones (including anabolic steroids), etc., that typically are present in samples at concentrations on the order of $10^{-8}$ to $10^{-11}$M. All urine drug tests (drugs of abuse, typically $10^{-6}$ to $10^{-8}$M) are certainly well-within the capability of this technology.

One aspect of the present invention concerns the recognition that oligonucleotides can be used to both facilitate the labeling of molecules, and to enhance the possible resolution obtainable through CE. Indeed, in the case of protein analytes, oligonucleotide-based modifications, as with a fluorophore label on the one end and the antigen on the other provide a means for obtaining a highly successful separation of labeled antigen from antigen-antibody complex by the CE/LIF methods of the present invention. Model proteins and complex protein mixtures with pI values ranging from 4.0 to 11.0 can be separated using CE in less than 10 minutes in the presence of phosphate buffer with pH of between 4.0 and 9.0.

One means for accomplishing such labeling is by synthesizing control pore glass-3'(9-fluorennylmethoxycarbonyl-amino)-(dT)$_{10}$-5' amine. This reagent can be derivatized with 5-carboxytetramethyl-rhodamine succinyl ester (Molecular Probes, Eugene, Oreg.) to thereby attach tetramethylrhodamine (TMR) to the 3'-amino terminus of the reagent. The 5' terminus of the derivative can be joined to a desired antigen.

For β-phycoerythrin based fluorometric immunoassay by LIF-CE, the sensitivity for analytes are $10^{-11}$M, while that of the synthetic fluorophore such as tetramethylrhodamine, is approximately one order of magnitude lower. Multiple labeling of synthetic fluorophore can be used to provide an arithmetic amplification of LIF signal if they are spaced properly.

Once the immunoreaction has occurred, the reactants and products are subjected to CE under conditions sufficient to resolve the Ab-Ag complex. The CE separation technique for proteins provides a means to separate the bound and free species of the labeled antigen or antibody without the use of a solid support. The application of these separation techniques in conjunction with laser induced fluorescence detection to make possible the homogeneous immunochemical measurement of species at concentrations in the range of $10^{-9}$ to $10^{-10}$ M.

Normal CE can be generally separated into two categories based upon the contents of the capillary columns. In "fixed gel" CE, the capillary tube is filled with a suitable gel, e.g., polyacrylamide gel, and separation of the constituents of the sample is thus predicated by both the size and the charge of the constituents. Despite the speed of analysis, fixed gel CE has several disadvantages, notably, the unpredictability and non-durable nature of the gel material. These factors make fixed gel CE unacceptable in any setting where numerous analytical runs are conducted.

In the second form of CE (i.e. "open" CE), the capillary tube is filled with an electrically conductive buffer solution (Kim, J. W. et al., *Clin. Chem.* 39:689–692 (1993)). Most preferably, the buffer is 150 mM borate, pH 10.00±0.25; concentrations between about 70 mM and about 400 mM are, however, viable. As the molarity of the buffer increases, the temperature inside the column can increase, and thus, in situations where temperature effects upon the constituents are a factor, lower concentrations of the buffer should be utilized. However, it is to be understood that the disclosed protocol can be accomplished with any separation buffer used in conjunction with the separation of proteinaceous materials using coated or untreated columns.

The capillary tube is then ionized with a negative charge. Such ionization causes the capillary wall to become negatively charged, thereby attracting positive ions from the buffer. Because the electroneutrality of the solution must be maintained, any flow of positive ions towards the capillary wall will be accompanied by a similar movement of the buffer solution and the constituents of the sample. This electroosmatic flow provides a fixed velocity component which drives both neutral species and ionic species, regardless of charge, towards the cathode. The buffer in "open CE" is stable against conduction and diffusion. Accordingly, separations can be obtained in "open CE" that are quite similar to those obtained in gel-based electrophoresis Open CE has many desirable qualities for, e.g., clinical sample analysis: because the analysis does not involve a gel-filled column, the inherent limitations on the number of analytical runs that can be conducted with any particular gel-filled column are avoided; when the capillary column is untreated, the aura of unpredictability which can be associated with coated columns is avoided; the sample size is small (usually on the order of 5 to 200 μl of diluted sample); sample analysis time is fast, i.e. less than about 20 minutes; and the protocol lends itself to automation, thus decreasing the labor skills necessary for efficient and effective sample analysis. The capillary column may be coated on the outside (using, e.g., a polyimide material) for ease of handling.

While the methods of the present invention can use either untreated or coated columns, it is preferred that the columns be untreated. When untreated capillary columns are utilized, preferably the separation buffer is as disclosed in U.S. Pat. No. 5,120,413, herein incorporated by reference. Suitable columns are further disclosed by Guttman, A., U.S. Pat. No. 5,213,669; Burolla, V. P., U.S. Pat. No. 5,198,091; Shieh, C-. H., U.S. Pat. No. 5,098,539; all herein incorporated by reference.

In a direct immunoassay, where Ab* is in excess, the principle of an open tube capillary electrophoretic separation, regardless of whether treated or untreated capillaries are used, is based on the charge to mass ratio of the molecular species under the conditions selected for separation (buffer composition, pH, etc., without the use of additives such as methylcellulose or PVA etc.). The efficiency of separation between Ab* and Ab*-Ag complex readily accommodates the excess Ab* of the reaction. For protein antigen, chemical modification of Ab* with any molecule of multiple negatively or positively charged moieties or a large neutral molecule such as dextran should alter the charge to mass ratio sufficiently to facilitate the separation of Ab* from the Ab*-Ag complex. Modifications that introduce positive charge or that augment the positive charge of the Ab* are the most preferred method of facilitating the separation of Ab* from most serum proteins. The use of such modifications causes a sharper peak in CE under standard running buffers. Monoclonal antibodies with Fab fragment would be desirable for a well-defined chemical modification of antibody. For digoxin, a hapten of molecular weight 981, the binding of antibody such as Fab fragment may not allow a sufficient perturbation in Ab*-digoxin complex from Ab* to affect sufficient resolution. A competitive immunoassay would be the most desirable route using labeled digoxin. For example, digoxin could be labeled with a fluorophore having a molecular weight of approximately 500 and which would ideally be a small molecule containing two sulfonyl or carboxyl groups after labeling. The charge to mass ratio of such an Ag* will be 2/1500 or 1/750 and as such will effectively be separated from Ab-Ag* by CE under appropriate buffer conditions. A net positively charged Ag* may be a practical alternative.

The presence of the label is preferably determined by automated or semi-automated means. In the preferred embodiment, wherein a fluorophore is used, the detection is mediated using a laser-induced fluorescence ("LIF") detector. An exemplary detector would contain a 1–3 milliwatt helium neon laser (543.5 nm) suitable for exciting the fluorophore. A suitable 2.5 milliwatt green helium-neon laser emitting at 543.5 nm is available from Particle Measuring Systems, Boulder, CO. The laser output is preferably filtered using a laser line filter and is focused into the detection region of the separation capillary. In a preferred embodiment, the detection system will be integrated into the P/ACE™ system using a laser headcoupler to a standard SMA-905 fiber connector to the P/ACE system with LIF detector (available from OZ Optics, Ontario, Canada). The fluorescent emission is preferably collected and collimated using a parabolic reflector which holds the capillary at its focus, and a scatter mask is preferably placed across the front of the parabola in the plane of intense laser scatter. The collimated emission is passed first through a notch filter (543.5 nm blocking), then through a 9 nm band pass filter centered at 580 nm (such filters are available from Barr Associates, Westford, Mass. and from Oriel, Stratford, Conn.). Detection is preferably accomplished using an end-on type photomultiplier tube (such as R374, Hamamatsu).

Macromolecules (such as proteins in serum) can be assayed using the above strategy. An antigenic determinant portion of a specific protein can be used for competitive immunoassays. Thus, for example, a monoclonal antibody specific to ferritin can be used to locate its corresponding antigenic determinant. A tryptic digestion of the ferritin would result in many peptide fragments. The single fragment bound to the monoclonal antibody may be spotted and sequenced. Synthetic peptide containing this antigen fragment can be labeled with fluorophore as the competing species of ferritin for the specific monoclonal antibody. Analysis and modification of labeled small peptide is substantially easier than that in protein. Indeed, as long as the dissociation constant of Ab-Ag complex is comparable to or lower than that of the antigen concentration, the above method will perform well.

Capillary electrophoresis instrumentation systems that can be used in conjunction with the present invention are well known. A particularly preferred instrument is a multichannel apparatus that allows simultaneous evaluation of at least two different aliquots of sample; more preferably, the apparatus has the capability of analyzing several aliquots simultaneously such that multiple electropherograms can be obtained and compared. A particularly preferred capillary electrophoretic system is disclosed in co-pending U.S. Ser. No. 07/916,308 entitled "Multichannel Automated Capillary Electrophoresis System" by Gerald L. Klein, which is incorporated herein by reference.

A particularly preferred capillary electrophoretic system is the P/ACE™ high performance capillary electrophoresis system (Beckman Instruments, Inc.) (Chen, F-. T. A., *Clin. Chem.* 38:1651–1953 (1992); Chen, F-. T. A., *J. Chromatogr.* 559:445–453 (1991); Fu, P. C. et al., *Clin. Chem.* 37:970 (1991); Chen, F-. T. A., *Clin. Chem.* 37:1061 (199); Gordon, M. J. et al., *Anal. Chem.* 63:69–72 (1991), all also herein incorporated by reference). Such instruments are most preferred in that normalization of the electropherograms can be accomplished via on-board computer software (such as System Gold™ software (Beckman Instruments, Inc., Fullerton, Calif., USA).

The CE immunoassay method of the present invention, when combined with LIF signal detection is capable of assaying analytes at concentrations of $10^{-9}$ to $10^{-10}$M. Indeed, the CE/LIF system described herein exhibits detection limits in the $10^{-12}$ to $10^{-11}$M range for the best known fluorophores (fluorescein, tetramethylrhodamine, and "BODIPY" labeled oligonucleotide for example). CE/LIF immunoassay formats thus meet the requirements of most clinical assays. The use of such fluorophores in combination with high sensitivity laser induced fluorescence (LIF) detectors thus permit the detection of analytes at concentrations that are 4–6 orders of magnitude lower than can be detected by measuring optical absorbance. Detection limits in this range permit many applications that were not previously possible or practical.

II. The Uses of the Present Invention

The capacity to measure such minute concentrations of analytes permits the CE/LIF method of the present invention allows many applications in conjunction with CE using well-defined substrates. DNA sequencing using fluorophore labeled primer and immunoquantitation by fluorophore labeled antigen or antibody are few examples. Both methods rely on using a labeled molecule to interrogate a specific chemical reaction. Labeled oligonucleotides or immunochemicals are applicable to many DNA-based probe chemistries as well as to food and environmental chemistries where trace contaminants and most of the assay procedures are cumbersome and difficult to perform.

A. Diagnostic Applications

Tissue damage and metabolism result in the leakage of enzymes into the peripheral circulation. Early detection of a tissue-specific enzymatic activity in blood is thus a highly significant indicia in diagnostic medicine. Most of the clinical analyses of enzymatic activities are predicated upon enzyme concentrations of $10^{-8}$ to $10^{-9}$M. Since enzymes have typical substrate turnover rates of about $10^3$ molecules per minute, an enzymatic assay to detect peripheral circulating enzymes would require approximately 10 minutes in order to generate the $10^{-4}$ to $10^{-5}$M concentration of product that would be needed to ensure spectrophotometric detection.

Unfortunately, such assay conditions cannot always be attained. A large number of clinically relevant enzymes are found in the circulation at significantly lower concentrations than $10^{-8}$ to $10^{-9}$M. Analyses of such enzymes thus require substantially longer incubation periods. In other instances, the substrates or products of the enzymatic reaction are unstable in aqueous solution. The slow hydrolysis of substrate can increase the background levels of the assay. Such factors make the clinical measurement of a relatively low enzymatic activity a time-consuming, cumbersome and error-prone process.

Through the use of the CE/LIF embodiment of the present invention, however, the measurement of $10^{-13}$M concentration of an enzyme can be readily achieved with short incubation periods. For example, angiotensin converting enzyme (ACE) (which catalyzes the cleavage of angiotensin I to angiotensin II) and renin (which catalyzes the cleavage of angiotensinogen to angiotensin I) regulate angiotensin I and II levels in blood. The levels of these enzymes in the circulation are responsible for hypertension, and the enzymes are targets of several anti-hypertensive agents. One difficulty in defining and using such agents, or in diagnosing hypertension has been the inability to readily measure ACE and renin serum levels. The present invention however, can be used to measure ACE and renin concentrations by performing the CE/LIF assay using angiotensin I that had been labeled with a fluorophore at an N-terminal or other non-interfering site (I*) as a substrate for ACE. The hydrolytic product of the reaction would be angiotensin II* and histidylleucine. These products could be effectively separated from I* by CE and the label detected by LIF. Quantitation of enzyme activity can be derived from the product II* minus the background under a fixed time frame.

The CE/LIF method of the present invention can also be used to analyze lipoproteins that may be present at low concentrations. Such analysis can be accomplished using a lipophilc dye that fluoresces in lipid environment but which does not fluoresce in aqueous solutions.

B. Biotechnology Applications

Genetically engineered pharmaceuticals are typically proteins and are formulated either in an injectable form that requires reconstitution or, more commonly, in a liquid form. Protease contaminants and thermal denaturation are important causes for degradation of protein formulation, particularly under long term storage. Thus, the analysis of trace protease activity is extremely important. The present invention however, can be used to measure protease concentrations by performing the CE/LIF assay using a protein or peptide protease substrate that had been labeled with a fluorophore at one of its termini or at another non-interfering site. The hydrolytic product of the reaction could be effectively separated from the uncleaved substrate by CE and the label detected by LIF. Quantitation of enzyme activity can be derived from the product minus the background under a fixed time frame.

In a similar manner, the CE/LIF system may be used to assay Synthetase activity, restriction enzyme activity or DNA hybridization processes. For example, by employing lipophilic fluorescent molecules that fluoresce only if they are intercalated in double-stranded DNA, the CE/LIF method of the present invention can be used to quantitate DNA levels, or to facilitate the detection of hybridized molecules. Such a method has wide applicability for DNA probe-based technologies, especially where amplification of one probed species is theoretically equal to the number of nucleotides of the probe. Products of the above processes can properly be separated from the substrate by CE and monitored with LIF.

C. Food Toxins and Environmental Pollutant Applications

The analysis of food toxins such as $T_2$ toxin, aflatoxins, etc. is a matter of grave concern in agriculture and the food service industry. The methods of the present invention can be readily adapted to define highly sensitive assays for such toxins. Similarly, the present invention may be used to detect and quantify low-level organic environmental pollutants in air, water, or soil. Presently, such analyses typically require solid-phase extraction (SPE) followed by gas chromatography and mass spectroscopy. These procedures are cumbersome and expensive to perform. The CE/LIF methods of the present invention provide an alternative to such methods.

As indicated, evaluation of CE is typically visually oriented, i.e. the electropherograms of samples are evaluated to determine the presence of peaks. The areas beneath a peak corresponds to the concentration of the analyte being assayed. Typically, the electropherogram is derived by plotting detection units (such as fluorescence) on the vertical axis, and time of constituent traversal through the column to a detection region on the horizontal axis. Results can also be derived in terms of a unit value, typically derived from the areas bounded by the individual peaks.

In order to compare two electropherograms (or the comparative areas beneath the peaks), it is preferred that the electropherograms be normalized. Typically, normalization involves three steps: (1) baseline normalization; (2) absorbance normalization; and (3) time normalization.

Baseline normalization is typically accomplished by adjusting the electropherograms such that each has a common horizontal baseline; beneficially, this merely requires shifting upward or downward the entire electropherogram in the case where the initial baseline is below or above the zero axis, respectively. Baseline normalization allows for creation of a common horizontal axis.

Absorbance normalization is preferably accomplished by adjusting the electropherograms based upon the most prevalent protein component in serum, albumin, or with another protein calibrator. Typically, the electropherogram peak associated with calibrator is the "tallest" peak. By selecting a single absorbance maximum for the calibrator, all of the peaks within the electropherogram will be proportionately adjusted. Absorbance normalization thus rectifies differences in, for example, the respective amounts of sample being analyzed.

Time normalization is principally accomplished in order to place the resulting electropherogram results within a constant region. Preferably, this is accomplished by the use of two "markers" which are added prior to the analysis of the treated and untreated samples. The markers are selected such that they are capable of traversing the capillary column and being detected at respective times that bracket the detection times of the sample constituents. Thus, if the detected sample constituents are detected at different times (due to, e.g., variability in the amount of sample analyzed), the relative detection times of the two sets of constituents can be normalized using the markers.

Most preferably, the two markers are prepared as follows: 20 mg of dichlorobenzoic acid is dissolved into 40 μl of benzyl alcohol and this mixture is added to 100 ml of an appropriate buffered solution, such as ICS™ diluent (Beckman Instruments, Inc.). Aliquots of this solution are then added to the treated and untreated samples, such that they will contain the same relative concentrations of markers. During analysis, these markers traverse the column along with the sample constituents. The electrophoretic mobilities are such that the dichlorobenzoic acid peak will typically appear as the "first" detected peak, followed by the sample constituents, then followed by the "last" detected peak, benzoyl alcohol. Thus, the peaks attributed to the sample constituents are bracketed by the two markers.

In an alternative embodiment of such time normalization, the markers may be selected such that they will bracket the position of the analyte-antibody complex.

Time normalization, like absorbance normalization, is accomplished such that the relative areas beneath the individual electropherogram peaks remain the same; such normalization merely allows the two electropherograms to be accurately compared to each other. Methodologies for such time normalization are disclosed by F-. T. A. Chen, U.S. Pat. No. 5,139,630, which is incorporated fully herein by reference. Methods for improving signal-to-noise ratios in electropherograms are disclosed by Anderson, P. D., U.S. Pat. No. 5,098,536, herein incorporated by reference.

An alternative approach to the analysis, which is also visually oriented, is based upon the manner in which slab-gel IFE results are derived, i.e. bands at the location of the M-protein. Methods and apparati for converting electropherogram peaks into such bands are disclosed in co-pending U.S. Ser. No. 07/911,307 entitled "Method and Apparatus for Displaying Capillary Electrophoresis Data" by Gerald L. Klein and Steven P. Katzman, which is incorporated herein by reference.

Having now generally described the invention, the same will be more readily understood through reference to the following examples which are provided by way of illustration, and are not intended to be limiting of the present invention, unless specified.

EXAMPLE 1

PROTEIN SEPARATION BY CE IN PHOSPHATE BUFFERS

Phosphate offers a wide range of buffer pH and is transparent in the UV region over the pH range of 2 to 12. Capillary electrophoresis was conducted in order to characterize its capacity to separate proteins.

Phosphate buffers at pH values between 4 and 10 were prepared by mixing the appropriate amounts of 0.4 or 0.5M mono-, di- and/or tri-sodium phosphate. The buffer used for serum protein separation was a borate based protein analysis buffer (Beckman Instruments, Inc.). All buffers were filtered through 0.45 μm filters before use. Protein standards were obtained from Sigma Biochemicals (St. Louis, Mo.) and Serva Biochemicals (Westbury, N.Y.). Protein or serum samples were dissolved or diluted in a sample diluent buffer containing 0.01% sodium azide, 75 mM sodium chloride, and 20 mM potassium phosphate at pH 7.0 (PBS). Each protein concentration was between 0.3 and 1 mg/ml. Fresh egg white was diluted 1 to 50 in PBS. Dimethylformamide (DMF) at 0.002 % v/v was added to the sample diluent as an electroosmotic flow marker (EOF).

Capillary electrophoresis was conducted using a P/ACE™ 2100 system (Beckman Instruments, Inc., Fullerton, Calif.), with P/ACE system software controlled by an IBM PS/2 model 55 SX. Post-run data analysis was performed on System Gold™ software by Beckman Instruments Inc., Fullerton, Calif. A capillary column, typically of 25 cm length (18.5 cm to detector window)×20 or 25 μm i.d. (Polymicro Technologies, Phoenix, Ariz.) was assembled in the P/ACE cartridge format (50×200 μm aperture). On-line detection by UV absorbance was at 200 nm. The capillary was maintained at ambient temperature during electrophoresis (usually 23° C.) with circulating coolant surrounding the capillary. Samples were introduced by pressure injection (0.5 psi) for 15 to 30 seconds. Electrophoresis was performed at the voltage shown in each electropherogram. Between runs, the capillary was sequentially washed with 1.0N sodium hydroxide and water (12 seconds of high pressure, 15 psi, rinsing each), followed by reconditioning with the running buffer (1 to 3 minutes of high pressure, 15 psi, rinsing).

Figure 1A:
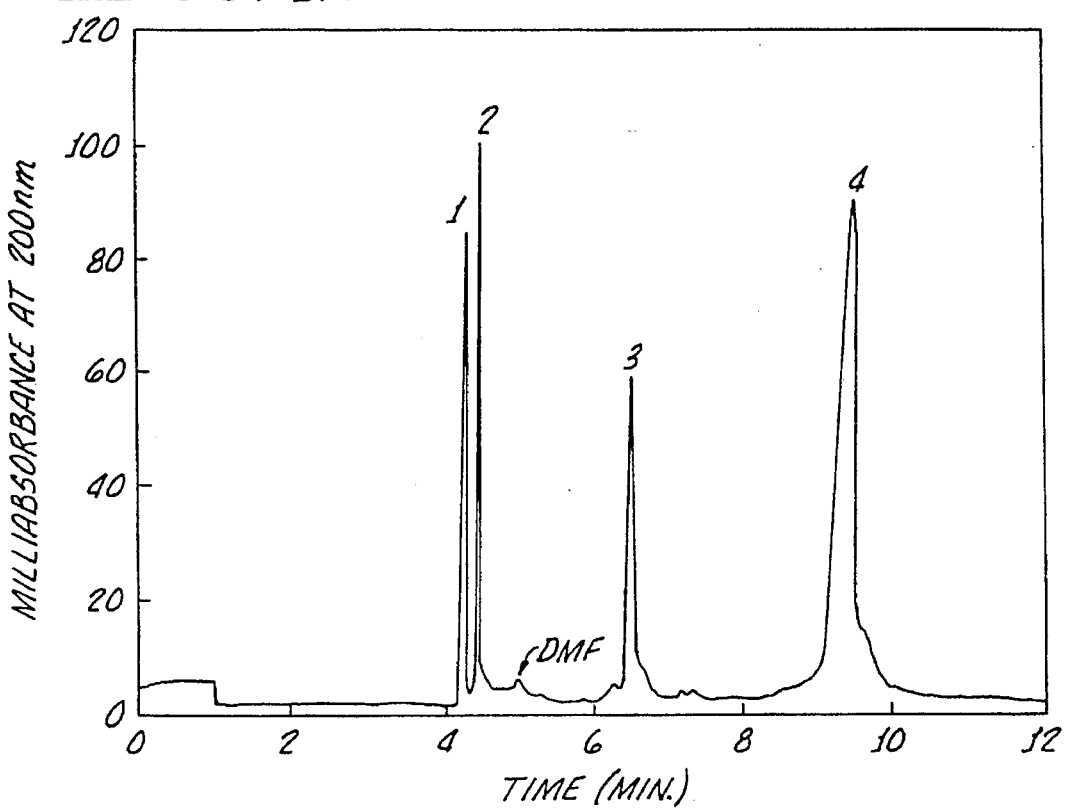
FIG. 1A shows an electropherogram of model proteins with 0.5M phosphate, pH 7.0. Conditions: Untreated fused-silica capillary, 25 μm (i.d.)×23 cm; Applied potential, 10 kV/53 μA; Peaks: 1=Trasylol; 2=cytochrome c; 3=carbonic anhydrase and 4=soy bean trypsin inhibitor.
Figure 1B:
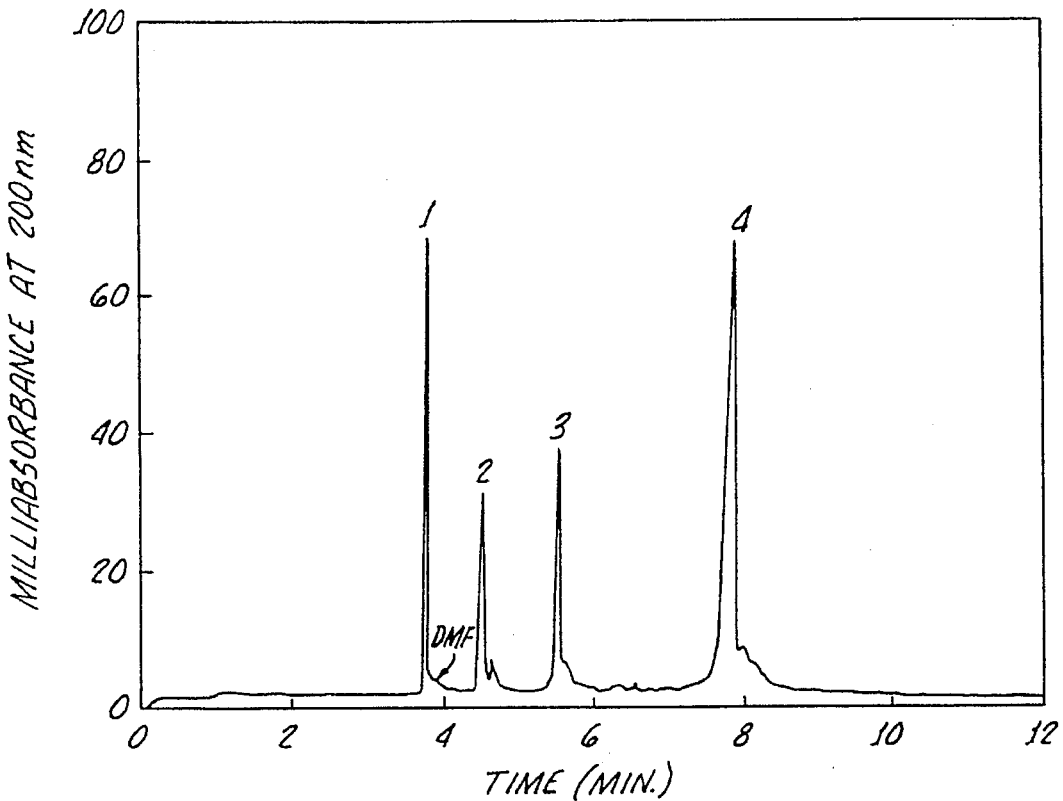
FIG. 1B shows an electropherogram of model proteins with 0.5M phosphate buffer, pH 9.0 (adapted from FIG. 2C of ref. 13). Conditions: Untreated fused-silica capillary, 25 μm (i.d.)×23 cm; Applied potential, 10 kV/75 μA; Peak i.d.; same as FIG. 1A.

FIGS. 1A and 1B show the separation of four model proteins with a 0.5M phosphate buffer at pH 7 and 9, respectively. Table 1 lists the proteins and their respective pI's. At a buffer pH of 7.0, bovine lung trypsin inhibitor (peak 1) and cytochrome C (peak 2) migrate earlier than the electroosmotic flow marker (DMF), while carbonic anhydrase (peak 3) and soy bean trypsin inhibitor (peak 4) migrate slower than DMF as anticipated. At a buffer pH of 9.0 (FIG. 1B, however, cytochrome C (peak 2) migrates after DMF and behaving like an anion instead of the cation as expected from its pI of being 10.65.

TABLE 1

| Proteins | pI | Molecular Mass |
| --- | --- | --- |
| Trasylol, Bovine lung | 10.50 | 5,000 |
| Cytochrome c | 10.65 | 12,000 |
| Carbonic anhydrase | 5.9 | 29,000 |
| Soybean trypsin inhibitor | 4.5 | 21,000 |
| Horse heart myoglobin | 7.0 | 17,500 |
| Conalbumin | 6.6 | 77,000 |
| β-lactoglobulin B | 5.4 | 35,000 |
| β-lactoglobulin A | 5.2 | 35,000 |
| Lysozyme | 11.0 | 14,000 |

The abnormal migration behavior of cytochrome C at phosphate buffer pH 9.0 in CE is presumably due to the solvation of the positively charged moieties of cytochrome C by the phosphate, moving as a solvation complex. Similar protein migration behavior was observed by Swedberg, S. A. (Anal. Biochem. 185:51–56 (1990)) using 0.5M phosphate buffer of pH 7.0, in a pentafluoro-benzoyl coated capillary.

Figure 2:
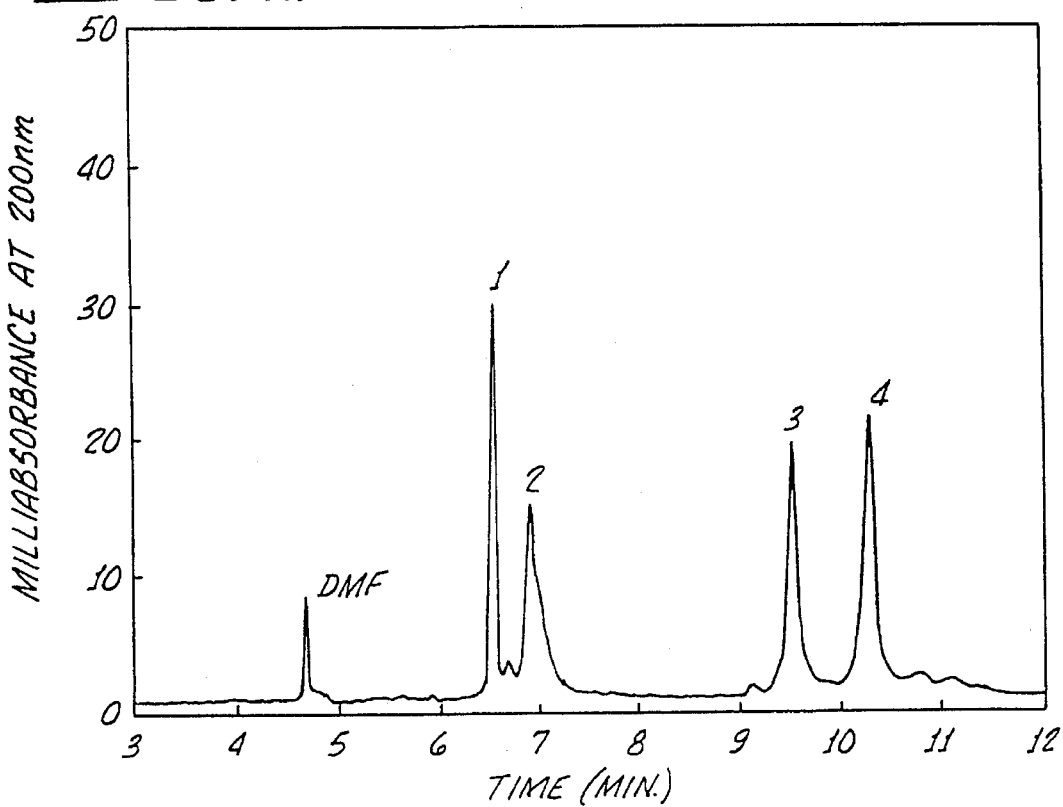
FIG. 2 shows an electropherogram of model proteins with 0.5M phosphate buffer, pH 8.0. Conditions: Untreated fused-silica capillary, 25 μm (i.d.)×23 cm; Applied potential, 10 kV/64 μA; Peaks: 1=myoglobin; 2=conalbumin; 3=β-lactoglobulin A; 4=β-lactoglobulin B.

FIG. 2 shows the separation of myoglobin, conalbumin, and β-lactoglobulin A and B with the 0.5M phosphate buffer at pH 8.0. Myoglobin and conalbumin, with pI values of 7.0 and 6.6, respectively, are well separated while β-lactoglobulin B and A are well-resolved. The separation of similar protein mixtures using buffers containing nonionic surfactant has also been achieved with a fused-silica capillary derivatized with octadecyltrichlorosilane (Towns, J. K. et al., Anal. Chem. 63:1126–1132 (1991)). Protein species with pI differences of only 0.2 can be well separated by CE under the present buffer conditions, indicating the general utility of the buffer system without resorting to the use of a coated capillary.

Between runs, the capillary was washed with base and water, followed by extensive rinsing with the running buffer. Nine consecutive runs were carried out with the protein mixture used for FIG. 2 and with a buffer pH of 8.0 in a 25 μm×23 cm capillary. Table 2 displays the reproducibility of the migration time, peak height and integrated area of each peak.

TABLE 2

| Protein | Time (min) | RSD (%) | Area | RSD (%) | Height | RSD (%) |
| --- | --- | --- | --- | --- | --- | --- |
| DMF (marker) | 4.66 | 0.30 | — | — | — | — |
| Myoglobin | 6.53 | 0.92 | 2.03 | 1.81 | 2879.33 | 1.32 |
| Conalbumin | 6.92 | 0.53 | 1.86 | 2.33 | 1413.44 | 1.46 |
| β-lactoglobulin B | 9.46 | 0.39 | 2.30 | 0.93 | 1781.89 | 5.55 |
| β-lactoglobulin A | 10.22 | 0.37 | 2.69 | 0.68 | 1990.33 | 3.07 |

McCormick, R. (Anal. Chem. 60:2322–2327 (1988)) observed that 0.15M phosphate buffers at pH 1.5 to 5.0 appear to be extremely efficient in separating peptides and many protein species with Pi values from 5.0 to 11.0. In the presence of phosphate buffer at pH 3.0 or below, most proteins are positively charged while the silica surface is nearly neutral and is most likely partially ionized. As the buffer pH increases, the silica surface becomes ionized, creating a negatively charged surface. At a buffer pH of above 5.0, the protein separation efficiency began to deteriorate in phosphate buffer, presumably due to the adsorption of proteins on the silica wall. At a pH of 5.0, carboxylic acid moieties in proteins are partially ionized, while all the amino and guanidine groups are fully positively charged. The phosphate buffer at pH values of 5.0 or above and at concentrations of 0.15 to 0.25M simply does not provide enough charge repulsion to prevent the adsorption of proteins on the negatively charged silica surface.

Figure 3:
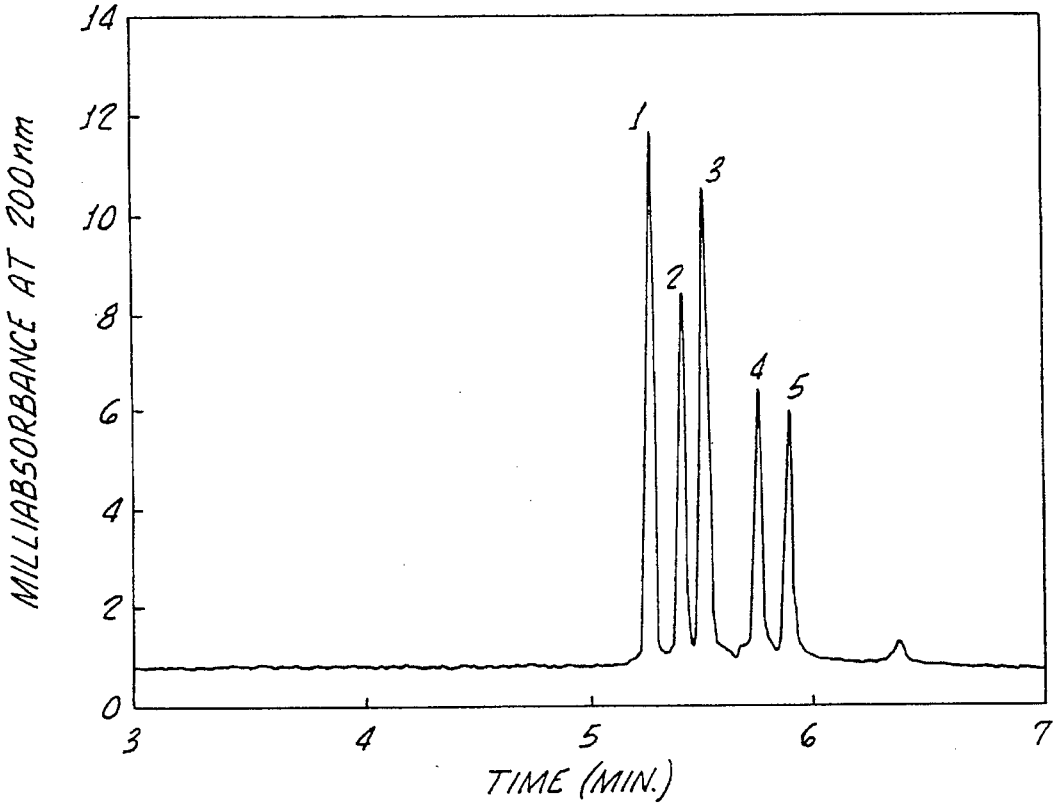
FIG. 3 shows an electropherogram of heart cytochrome c from various animal species. Conditions: Untreated fused-silica capillary, 20 μm (i.d.)×25 cm; Applied potential, 10 kV/34 μA; 0.4M phosphate buffer, pH 4.0. Peaks: 1=horse 2=Dog; 3=pig; 4=chicken and 5=tuna.

As indicated by the above data, a substantially higher concentration of phosphate was required to discourage protein interaction with the silica surface at pH values of 4.0 and above. An almost baseline resolution of cytochrome C from all five species may be obtained at pH 4.0 with 0.4M phosphate buffer. Lower buffer salt concentration at same pH simply yield broad unresolved electropherogram, indicating significant interaction between cytochrome C species and capillary wall (FIG. 3).

The mechanism proposed for using a high phosphate buffer for protein separations by CE in fused-silica columns is consistent with the ion-exchange mechanism proposed by Lauer, H. H. et al. (Anal. Chem. 58:166–169 (1986)) and Greene, J. S. et al. (J. Chromatogr. 478:63–70 (1989)). The solvation complex of proteins with phosphate results in the modification of the intrinsic protein charges (Swedberg, S. A., Anal. Biochem. 185:51–56 (1990)), consistent with the observed migration sequences of proteins relative to the electroosmotic flow marker.

Emerick, R. J. (Amer. Instit. Nutr. 22:1925–1928 (1987) observed that phosphate buffer at a pH value above 6.5 inhibits protein-silicic acid complex formation. Mitsyuk, B. M. et al. (Inorg. Chem. 17:471–473 (1972)) proposed the interaction of silica with phosphate to form a donor-acceptor type of complex. Such an interaction between the phosphate and the silica surface at a pH value of above 5.0 represents a dynamic coating phenomenon (McCormick, R., Anal. Chem. 60:2322–2327 (1988)) that may require a substantially higher phosphate concentration.

The use of high-ionic strength buffer in CE results in large currents that produce heat. The application of a small diameter capillary reduces the current. However, in most of the above applications, the voltage gradient was typically 300 to 400 V/cm, while the current varied from 30 to 75 μA. Thus, the CE system should include sufficient coolant circulation to provide efficient removal of this heat (Rush, R. S. et al., Anal. Chem. 63:1346–1350 (1991); Bello, M. S. et al., J. Chromatogr. 625:323–330 (1992)).

The applicability of capillary electrophoresis in uncoated fused silica capillaries has thus been demonstrated for the analysis of complex protein mixtures, such as serum, ascites fluid, urine and CSF. By using a buffer system containing a high concentration of phosphate, the protein analyses can be achieved rapidly, reliably and with excellent precision over a wide range of buffer pH. The use of a high ionic strength buffer in CE results in high currents, which produce Joule heating. The use of small diameter columns, and coolant circulation diminishes the heating effect.

The mechanism of protein separation using the phosphate buffer system is based on a dynamic interaction of phosphate ions with the silica surface and on the formation of solvation complex of proteins by phosphate anions to minimize protein-silica wall interactions. The experimental evidence shown here indicates a role of the dynamic coating phenomenon at neutral and basic pH. Most importantly, the present buffer system, with its broad range of operational pH, allows the selection of a proper buffer pH to provide an optimum separation of the protein species of interest.

EXAMPLE 2

PROTEIN SEPARATIONS IN BORATE AND BECKMAN PROTEIN ANALYSIS BUFFERS

Figure 4A:
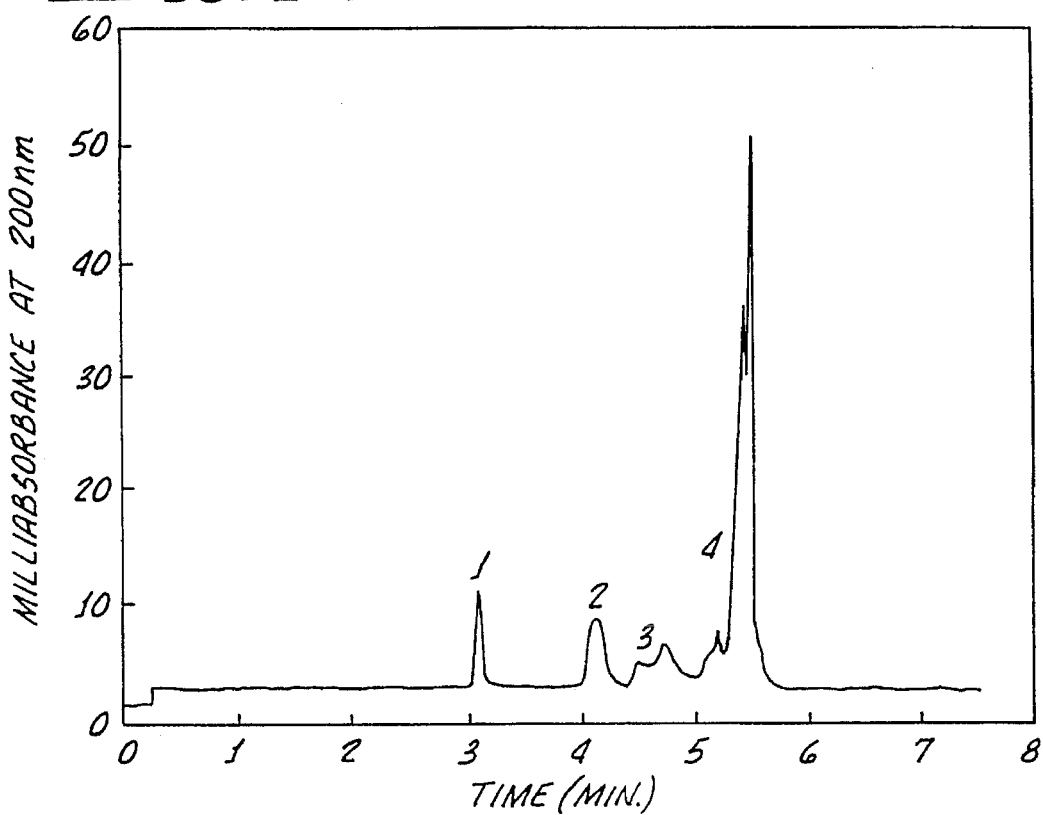
FIG. 4A shows an electropherogram of egg white proteins. Conditions: Untreated fused-silica capillary, 20 μm (i.d.)×25 cm; Applied potential, 10 kV/16 μA; buffer, 200 mM borate at pH 10.0. Peaks: 1=DMF and lysozyme; 2=conalbumin; 3=globulins; 4=ovomucoid and ovalbumin.

Capillary electrophoresis was conducted using the borate and Beckman protein analysis buffers described in Example 1. Borate based buffer at a pH of above 9.0 appeared to have broad application for the separation of many proteins. For example, egg white proteins could be resolved into four zones—conalbumin, globulins, ovalbumin and ovomucoid—as shown in FIG. 4A (200 mM borate, pH 10). Lysozyme peak in egg white is missing, presumably because it co-migrates with the neutral marker (DMF) or may be adsorbed by the capillary wall. Using an authentic egg lysozyme sample at 0.5 mg/ml for CE analysis under the identical running condition, lysozyme peak was absent, indicating an almost total adsorption on the capillary wall.

Figure 4B:
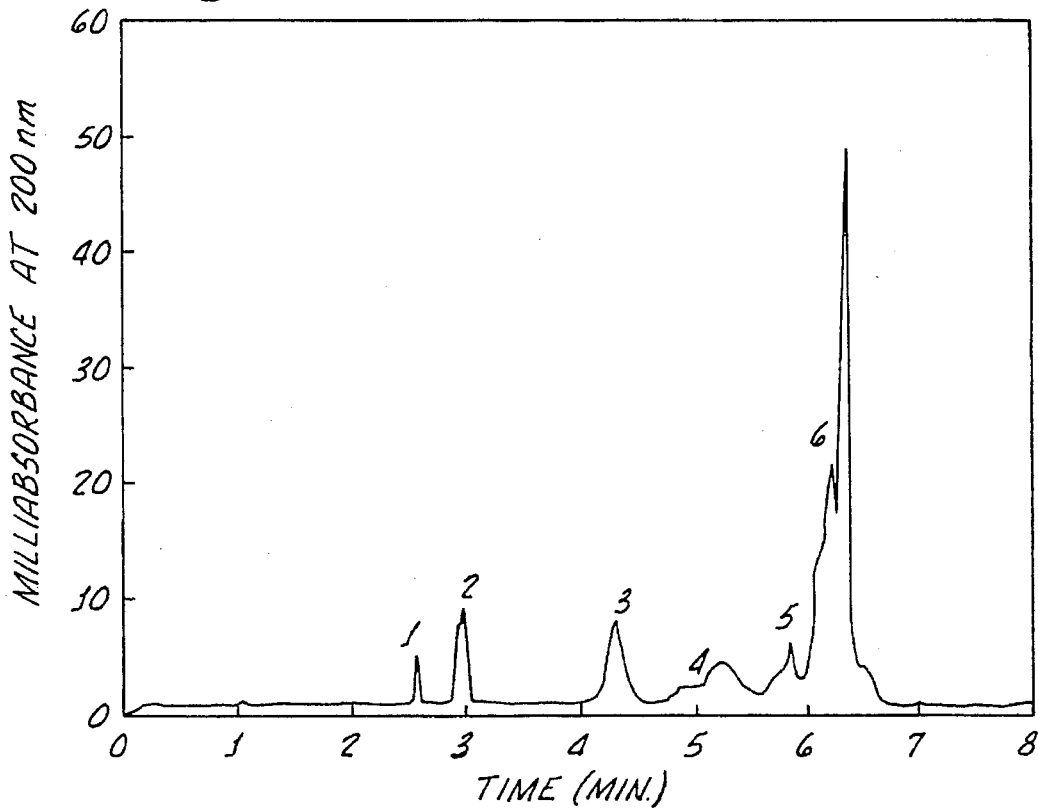
FIG. 4B shows an electropherogram of egg white proteins. Conditions: Untreated fused-silica capillary, 20 μm (i.d.)×25 cm; Applied potential, 12 kV/26 μa; 300 mM borate buffer, pH 10.0. Peaks: 1=lysozyme; 2=DMF; 3=conalbumin; 4=globulins; 5 and 6=ovomucoid and ovalbumin.

As the borate buffer concentration was increased to 300 mM, a well-defined separation pattern was obtained (FIG. 4B). Lysozyme was clearly observed at 2.6 minutes (ahead of the neutral marker, seen at 2.9 minutes), consistent with the isoelectric point of lysozyme at 11.0, which is 1.0 pH unit above the buffer pH. The high borate buffer prevents the adsorption of lysozyme, a very basic protein, on the silica surface (Chen, F-. T. A., *Clin. Chem.* 38:1651–53 (1992)). The remaining proteins migrated in order according to their respective isoelectric points. Ovomucoid (pI=4.6) appeared between 6 and 6.6 minutes, globulin (pI=5.5–5.8) migrated as two broad peaks at 5.2 and 5.35 minutes, and conalbumin (pI=6.6) at 4.3 minutes. Each protein peak was identified by co-injection with the authentic sample. Ovomucoid and ovalbumin are calculated to constitute 67%, the globulins are 13%, and conalbumin is 16% of the protein mixture, while lysozyme is a minor component at only 3.5%.

Figure 5A:
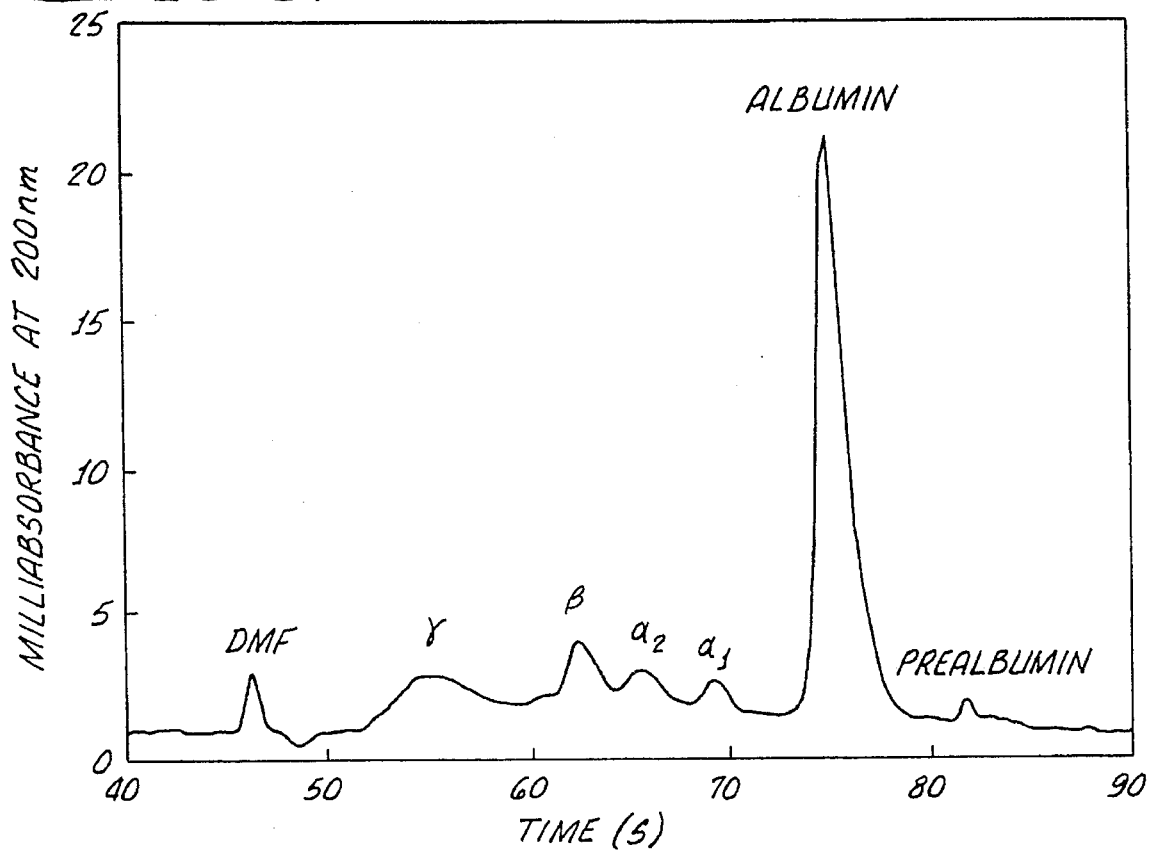
FIGS. 5A and 5B show capillary electropherograms of normal serum protein.
Figure 5B:
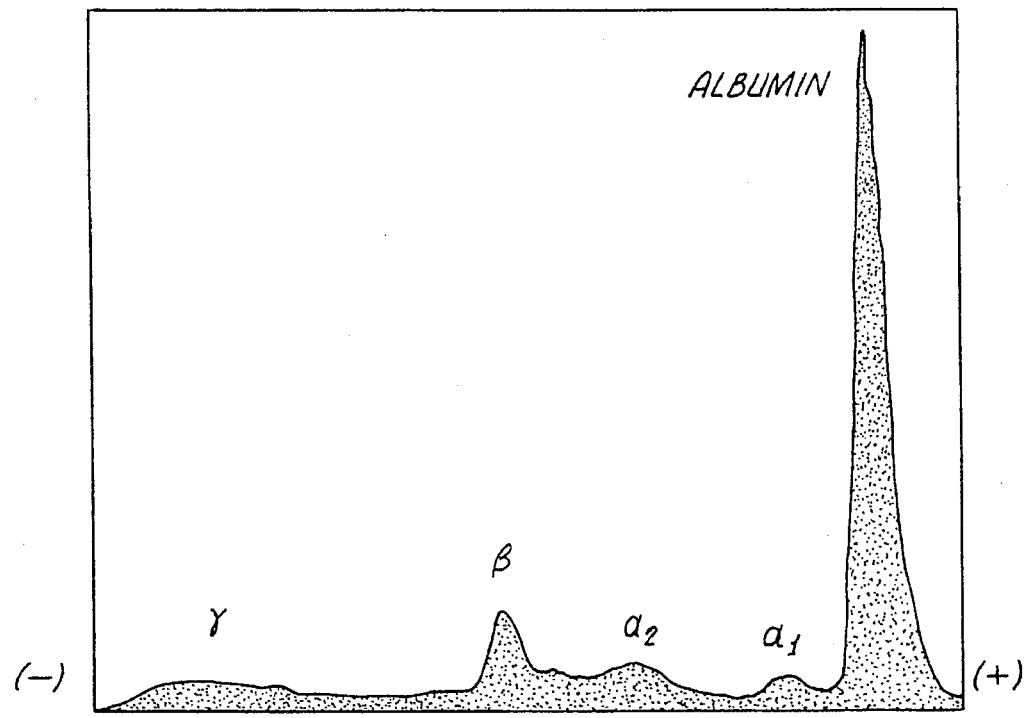

The feasibility of routine analysis of human serum proteins by CE has been indicated by Chen, F-. T. A. et al. (*Clin. Chem.* 37:14–19 (1991)) and by Gordon, M. G. et al. (*Anal. Chem.* 63:69–72 (1991)). Chen, F-. T. A. (*J. Chromatogr.* 516:69–78 (1991)) has demonstrated the advantage of using a capillary column with an inner diameter of ≦25 μm for rapid protein analysis. FIGS. 5A and 5B show normal human serum protein separation patterns: (FIG. 5A) by CE, using a 20 μm (i.e.) ×25 cm capillary with a voltage gradient of 800 v/cm using Beckman protein-analysis buffer, and (FIG. 5B) by agarose gel electrophoresis. Each of the serum protein fractions can clearly be identified. Gamma globulin appears first, followed by beta, alpha2, alpha1, albumin and a minute amount of prealbumin. A substantially better resolved serum protein separation can be obtained by using a higher ionic strength of the same buffer (Chen, F-. T. A., *J. Chromatogr.* 516:69–78 (1991); Chen, F-. T. A., *Clin. Chem.* 38:1651–53 (1992)). The addition of high salt to the buffer appears to minimize protein-protein interactions, which may be responsible for peak broadening in protein separations by CE in general.

Figure 6A:
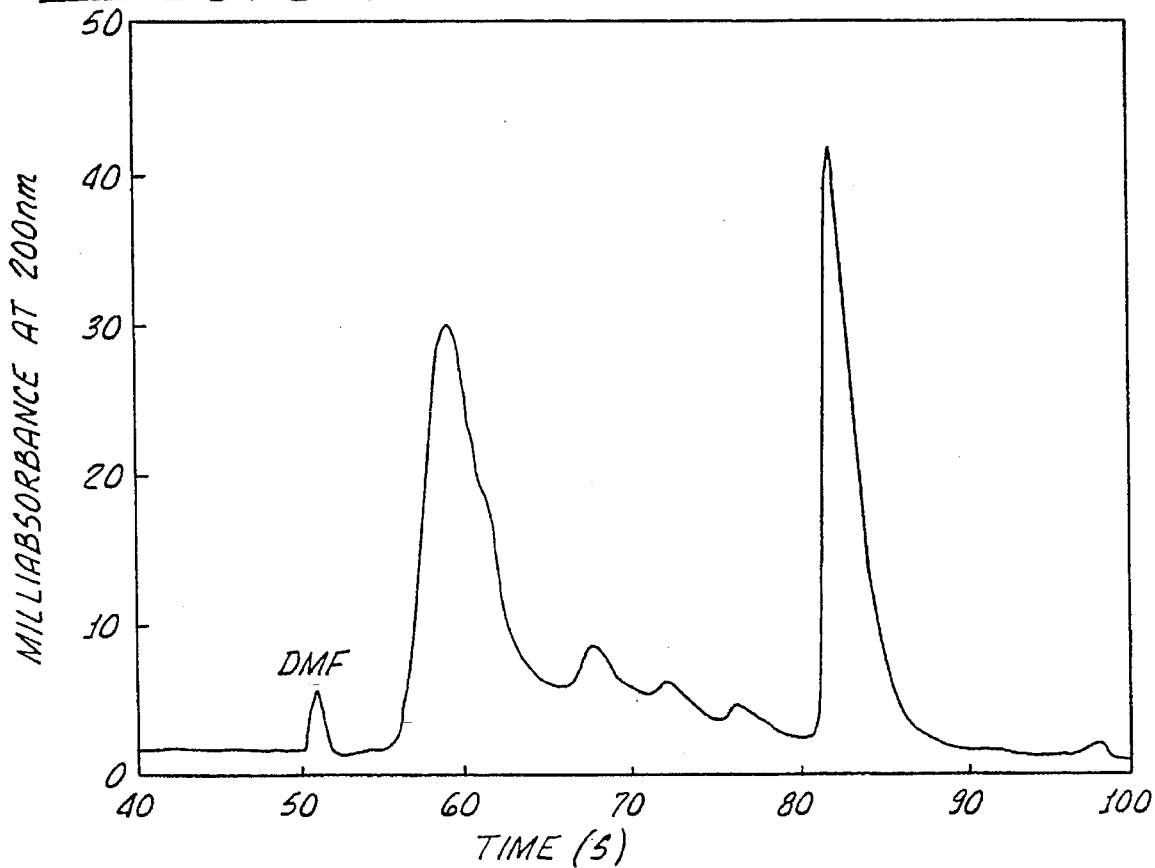
FIGS. 6A and 6B are analyses conducted on abnormal serum.
Figure 6B:
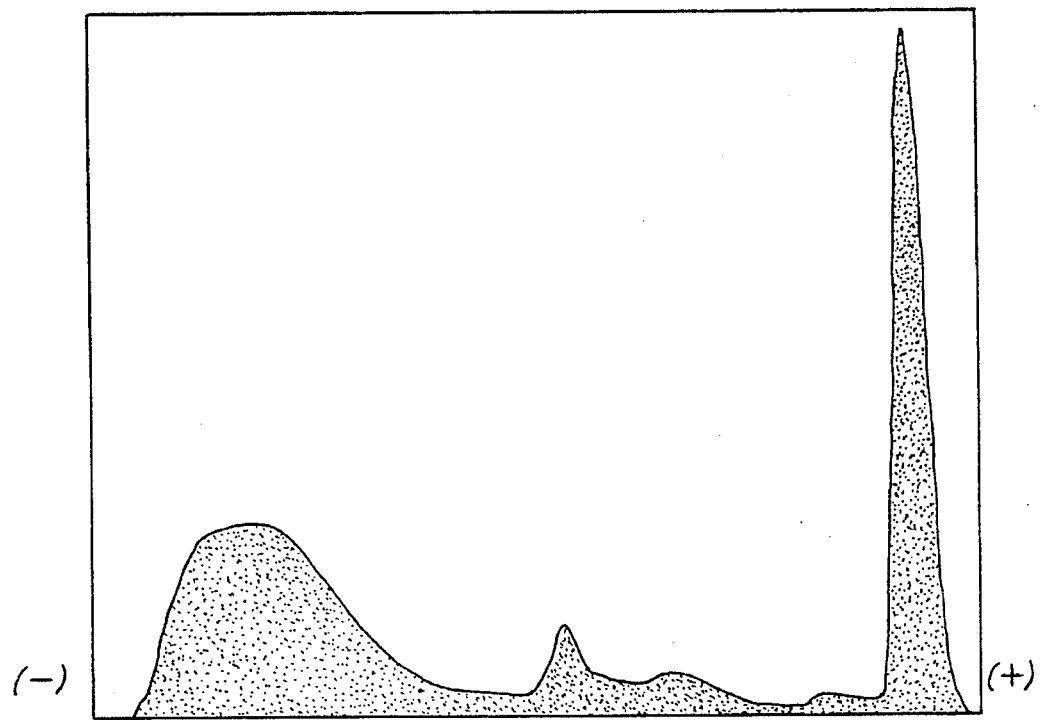
Figure 7A:
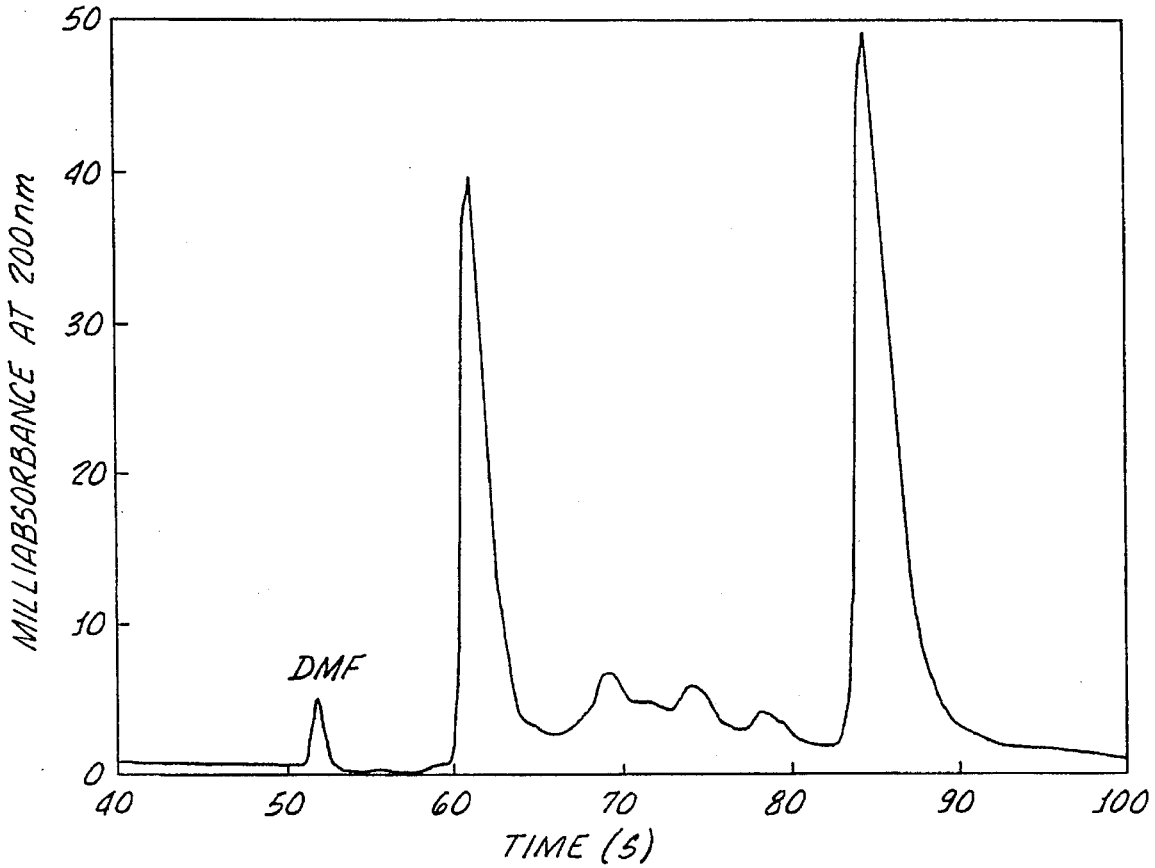
FIGS. 7A and 7B are analyses of protein from an IgG myeloma patient serum protein.
Figure 7B:
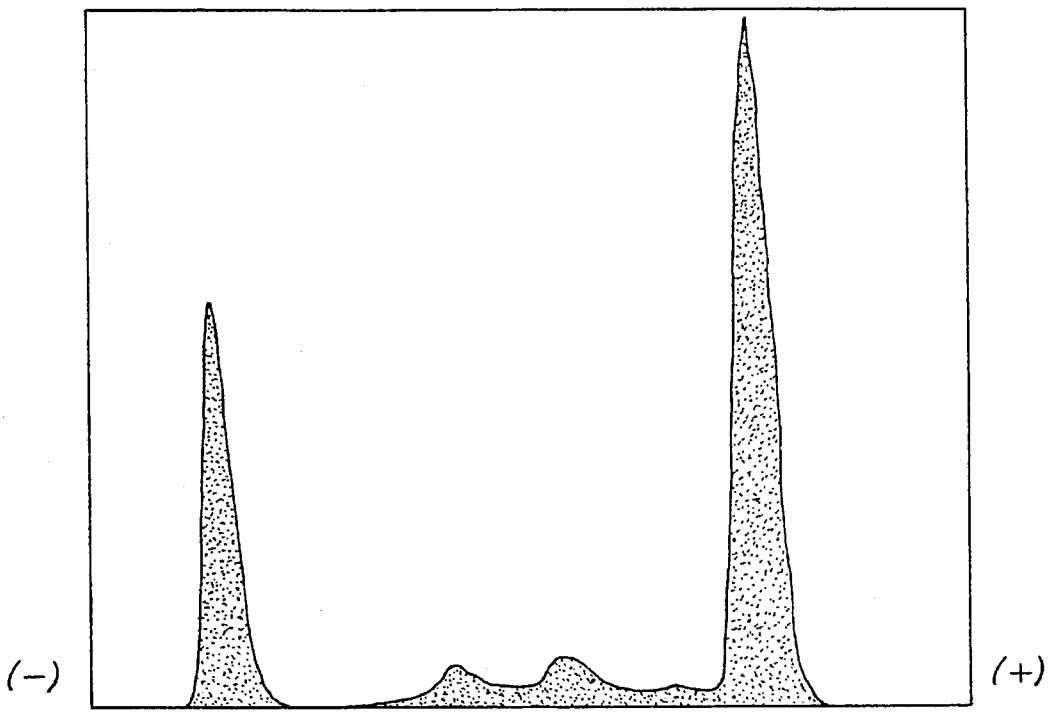

As indicated in FIGS. 6A and 6B, respectively, an abnormal control serum sample showed almost identical separation patterns by both the CE and the agarose gel electrophoresis methods. Serum sample from a myeloma patient was analyzed by both capillary and agarose gel electrophoresis systems for comparison and they exhibit almost identical patterns by the two methods, as shown in FIG. 7A (CE) and FIG. 7B (agarose gel electrophoresis).

Figure 8:
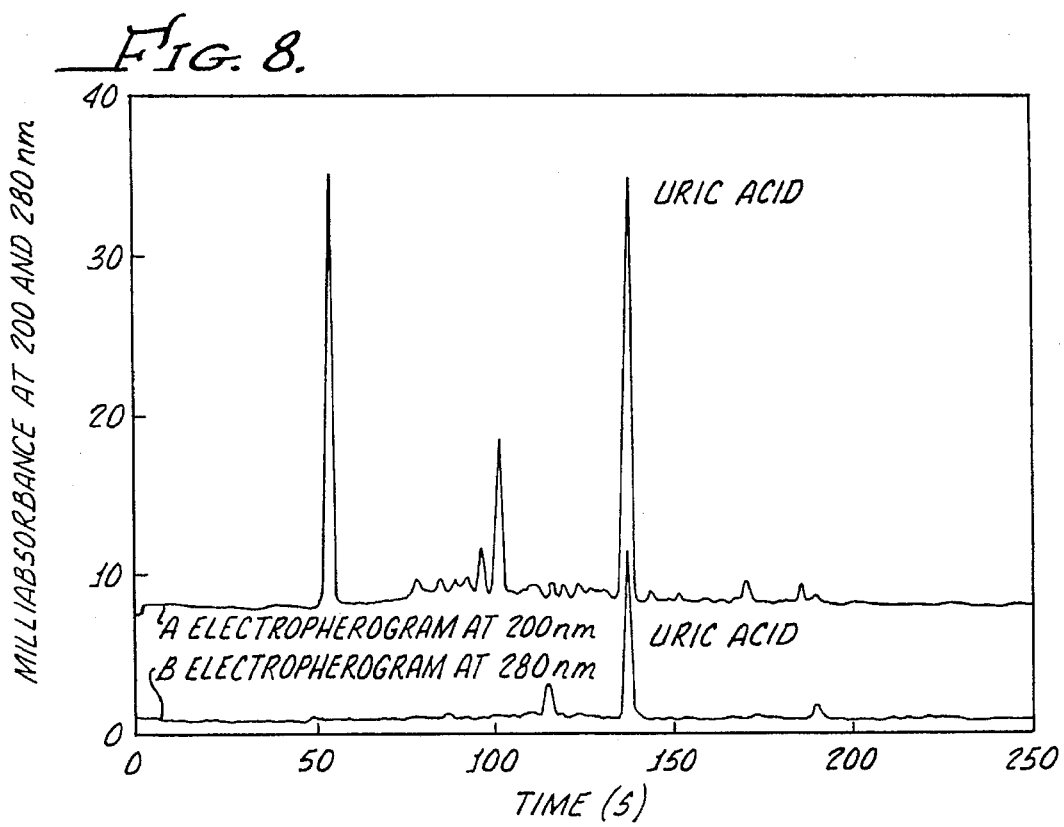
FIG. 8 shows capillary electropherograms of a normal urine sample performed at 200 nm (A), and at 280 nm (B). Conditions as in FIG. 5A.

The same borate based buffer system is also applicable to the analysis of urine specimen, which sample can be directly introduced into the CE system without preparation steps. The separation of proteins and all other ionic species is shown in FIG. 8, where a fairly complex pattern (A) was obtained by monitoring the absorbance at 200 nm. Small organic molecules, including creatinine, hippuric aid, nucleic acid degradation products and etc. could be identified. However, the pattern obtained using absorbance monitoring at 280 nm shows significantly fewer peaks. Uric acid can be identified as the major peak migrates at 137 seconds, as shown in (B) of FIG. 8. Proteins in urine would be expected to migrate between 55 and 100 seconds.

Figure 9:
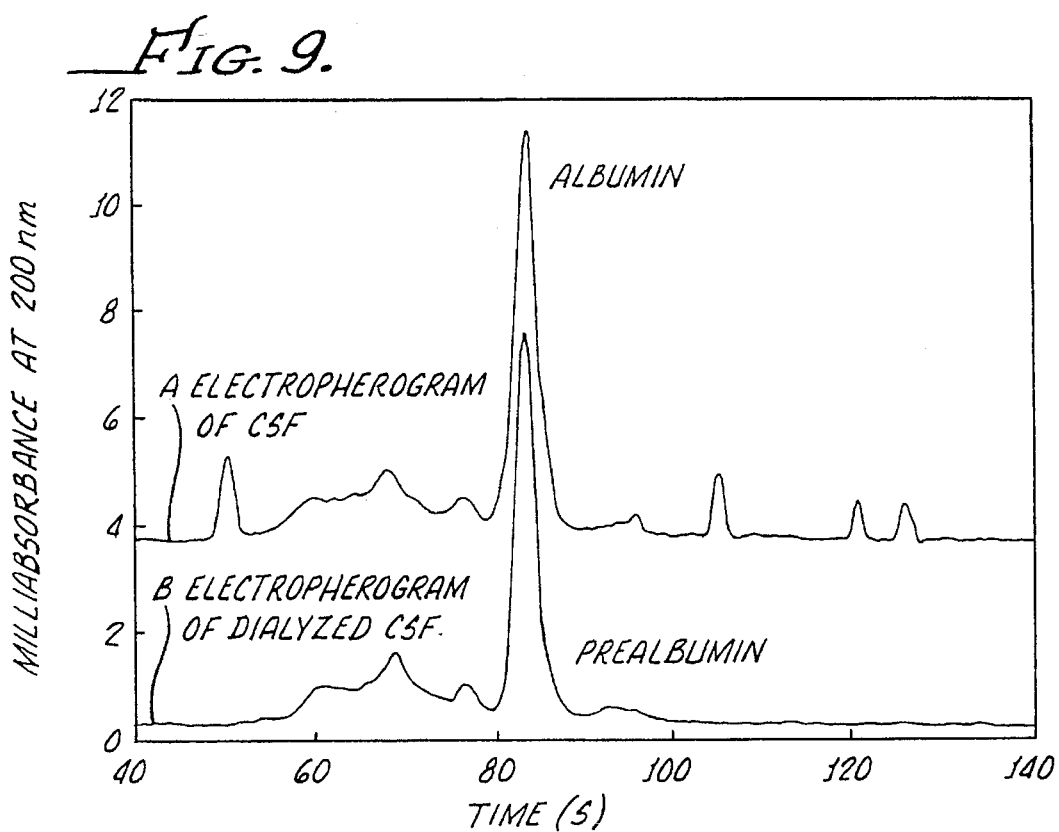
FIG. 9 shows capillary electropherograms of a patient CSF sample performed at 200 nm (A), and a dialyzed CSF sample (B). Conditions as in FIG. 5A.

Cerebrospinal fluid (CSF) presents many interesting CE separation patterns, as shown in FIG. 9. Here, as with urine, samples can be introduced in the CE system (A) without pre-concentration. The electropherogram in tracing (A) of FIG. 9 shows a normal protein separation pattern, including a distinct peak for prealbumin (confirmed by coinjection with pure prealbumin). The several peaks observed outside of the normal serum protein separation zones are presumably small molecules, which are detectable in CE, since they are not lost in the fixing and staining processes required for other gel electrophoresis techniques. Tracing (B) of FIG. 9 exhibits B the electropherogram of the same CSF sample after dialysis through a membrane having a molecular mass cutoff of 14 kd.

EXAMPLE 3

CE/LIF DETECTION OF DIGOXIGENIN

The competitive CE/LIF method of the present invention was used to measure digoxigenin levels in serum. Digoxigenin was labeled with β-phycoerythrin ("BP*"), incubated in the presence of limiting amounts of anti-digoxin Fab, and subjected to CE.

Digoxigenin labeled β-phycoerythrin (D-BP*) was synthesized by a reaction of digoxigenin-NHS with β-phycoerythrin at a 20:1 molar ratio in PBS in order to ensure that nearly every β-phycoerythrin molecule was labeled with at least one digoxigenin molecule. The stock solution of D-BP* was diluted in ICS diluent containing 2 mg/ml BSA. For the immunoreaction, 100 μl of a 1.0 μg/ml D-BP* solution was incubated with excess affinity purified Fab to digoxin (Boehringer Mannhein Corp.). Conditions were: 2 kV/10 s inj; 7 kV/74 μa.

The CE was conducted using a P/ACE system 2100 that had been modified by removing the UV absorbance detector and installing a LIF detector. A 1.0 milliwatt helium neon laser (543.5 nm) was used to excite the β-phycoerythrin label. The laser output was filtered using a 10 nm laser line filter and was focused into the detection region of the separation capillary using a 5 cm focal length plane convex lens. The fluorescent emission was collected and collimated using a parabolic reflector which held the capillary at its focus. A scatter mask was placed across the front of the parabola in the plane of intense laser scatter. The collimated emission was passed first through a custom made notch filter (543.5 nm blocking), then through a 9 nm band pass filter centered at 580 nm (both filters were purchased from Barr Associates), and finally onto the photocathode of an end-on type photomultiplier tube (R374, Hamamatsu). Human serum-based CE calibrators were used at concentrations of 0.42, 2.72 and 5.21 ng/ml.

Figure 10A:
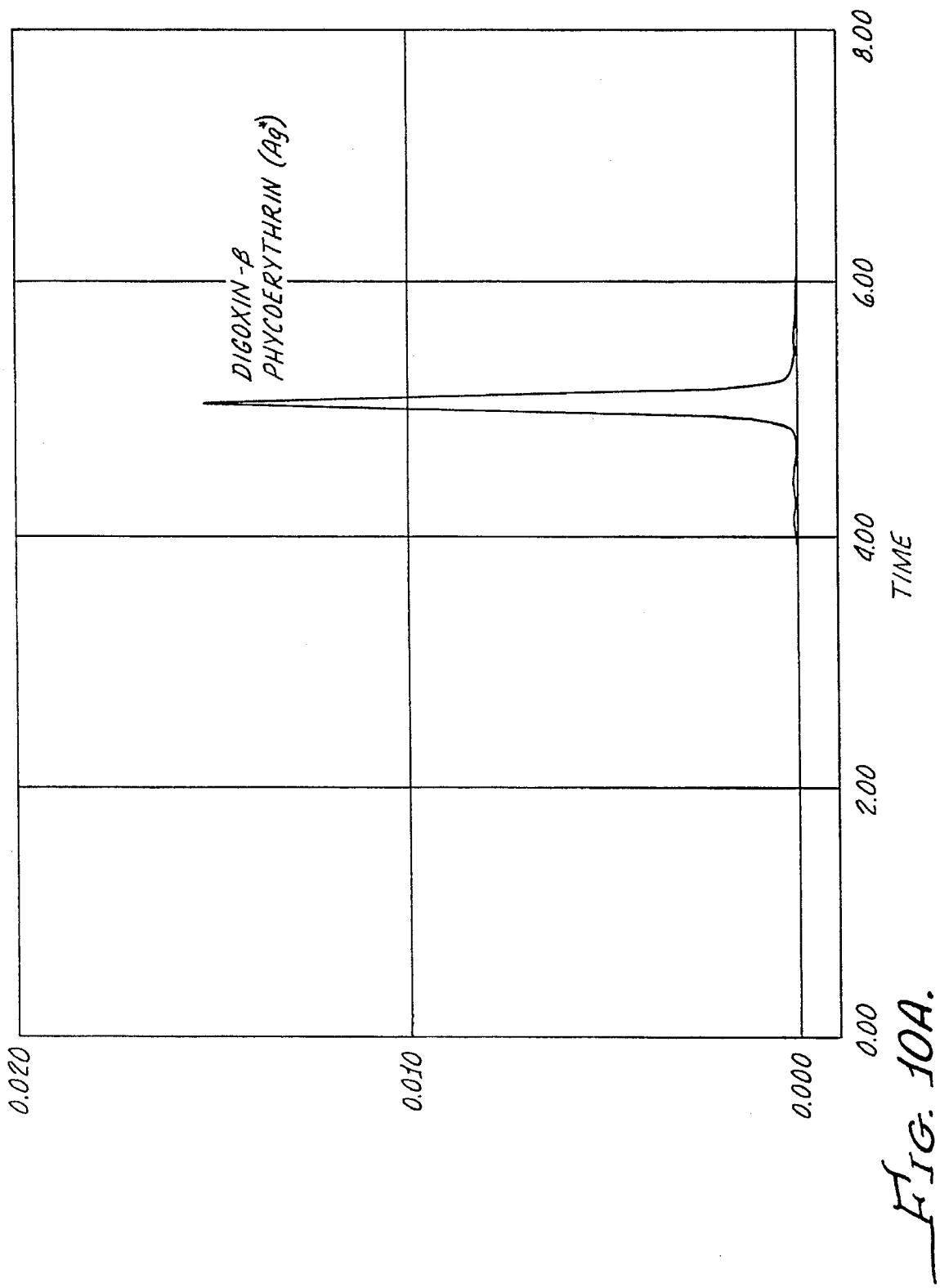
FIGS. 10A–10D show the ability of a competitive CE/LIF immunoassay to mediate the separation of species in reaction mixtures using 100 μL of labeled digoxigenin (1 μg/ml) and 0 μl of anti-digoxin Fab (FIG. 10A); 10 μl of 5 μg/ml anti-digoxin Fab (FIG. 10B); 50 μl of 5 μg/ml anti-digoxin Fab (FIG. 10C); 100 μl of 5 μg/ml anti-digoxin Fab (FIG. 10D).

When CE was performed in a 75 μm×32 cm capillary using the modified P/ACE with LIF detection (with green-He/Ne laser excitation at 543 nm) significant adsorption of D-BP* was observed at $10^{-5}$M which resulted in a broad D-BP* peak. At $10^{-6}$M or less, this D-BP* peak disappeared, presumably due to adsorption to the silica wall. Although the addition of albumin to the D-BP* did not markedly improve the detection, the use of D-BP* diluted in PBS containing purified immunoglobulins (0.5 mg/mL) did result in excellent peak symmetry and detection sensitivity as illustrated in FIG. 10A.

Figure 10B:
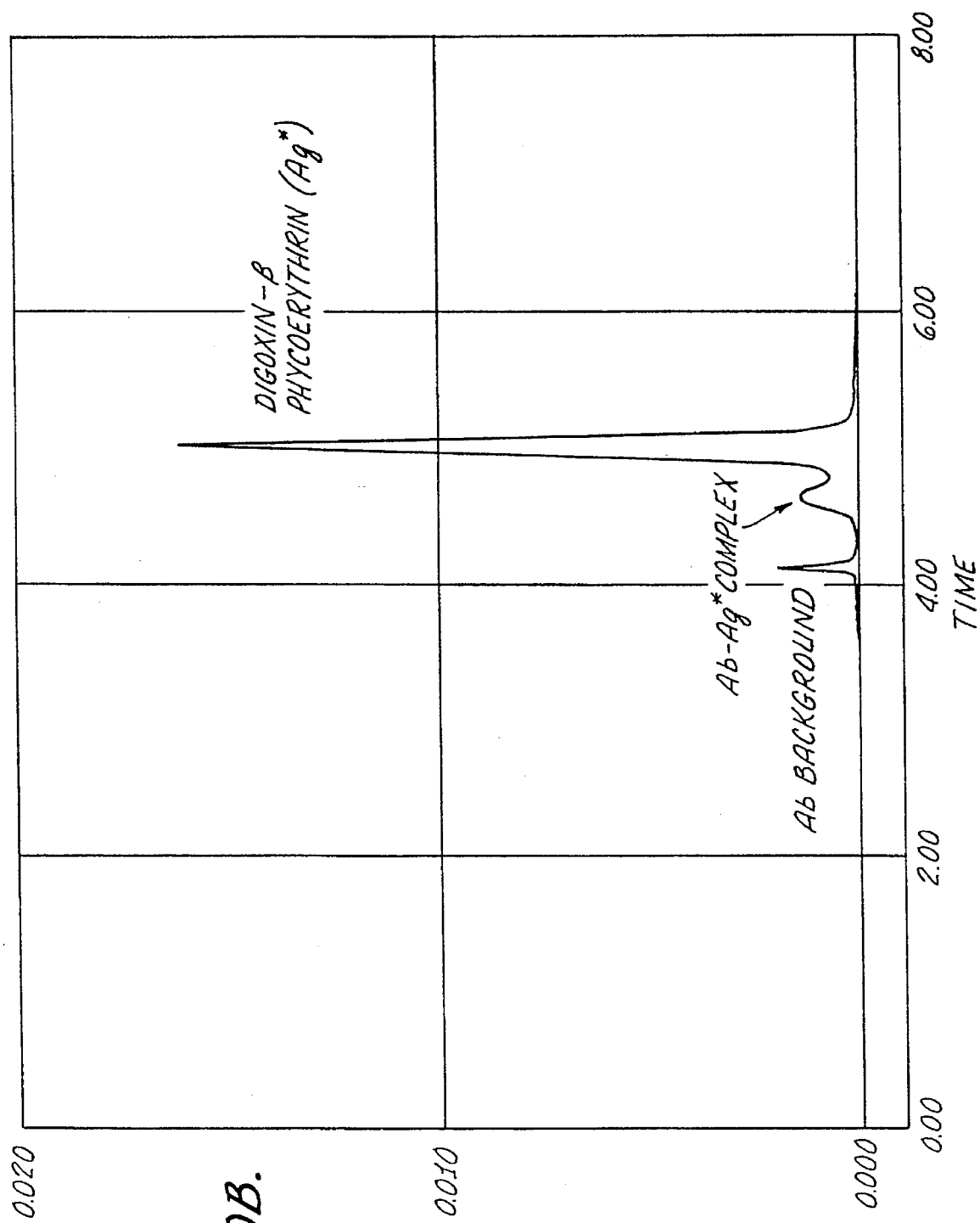
Figure 10C:
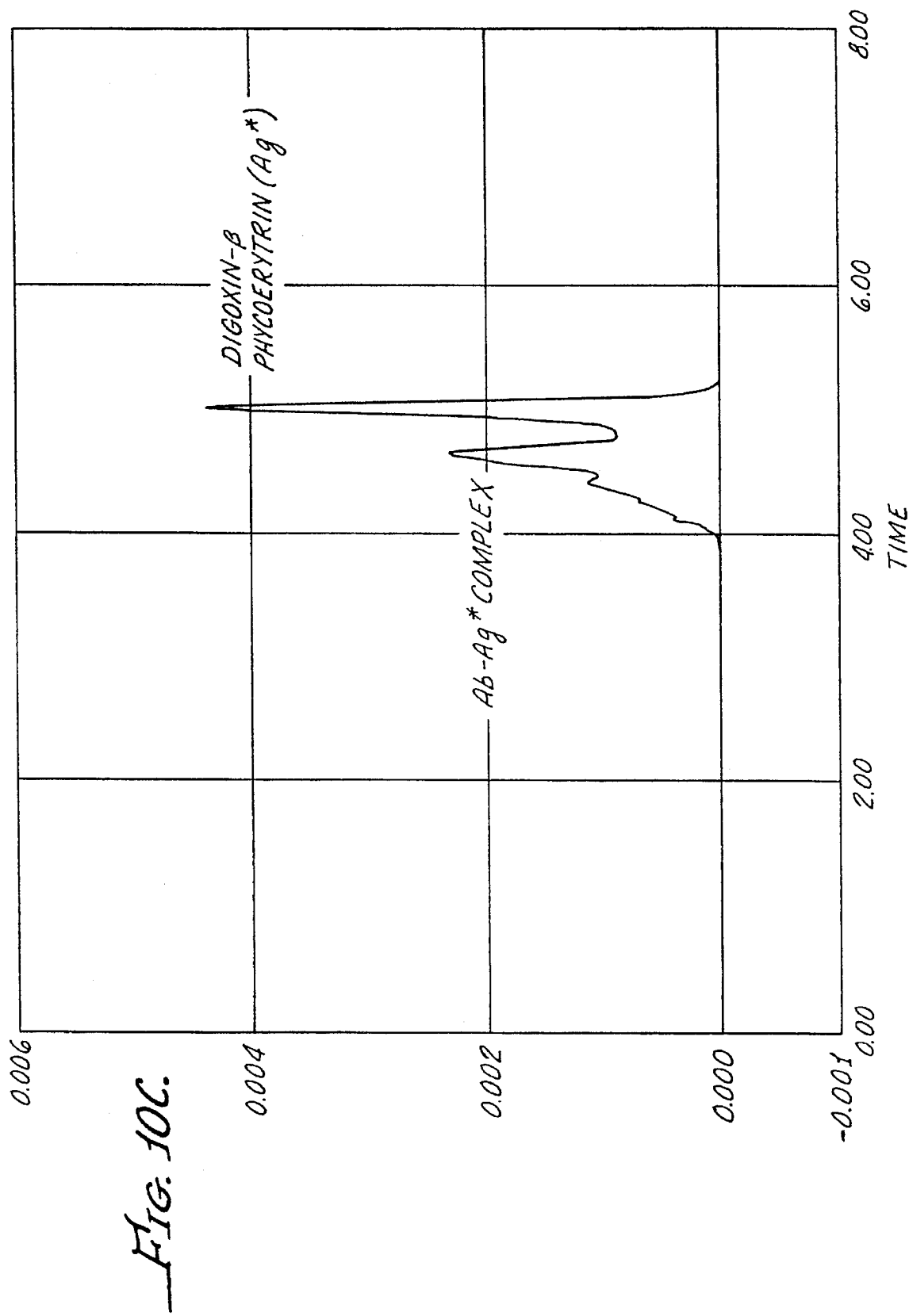

The capacity of the CE to distinguish the Ab-Ag* complex was determined by providing 10 μl of Fab, 50 μl of Fab, or 100 μl of Fab (solution was 5 μg/ml Fab) to the reaction. The electropherograms of these experiments are provided in FIGS. 10B, 10C and 10D, respectively. The experiment demonstrated that D-BP* exhibited good separation from the anti-digoxin Fab and D-BP* complex by CE (at $10^{-8}$M analytes using a 71 μm×32 cm capillary on the modified P/ACE).

Figure 10D:
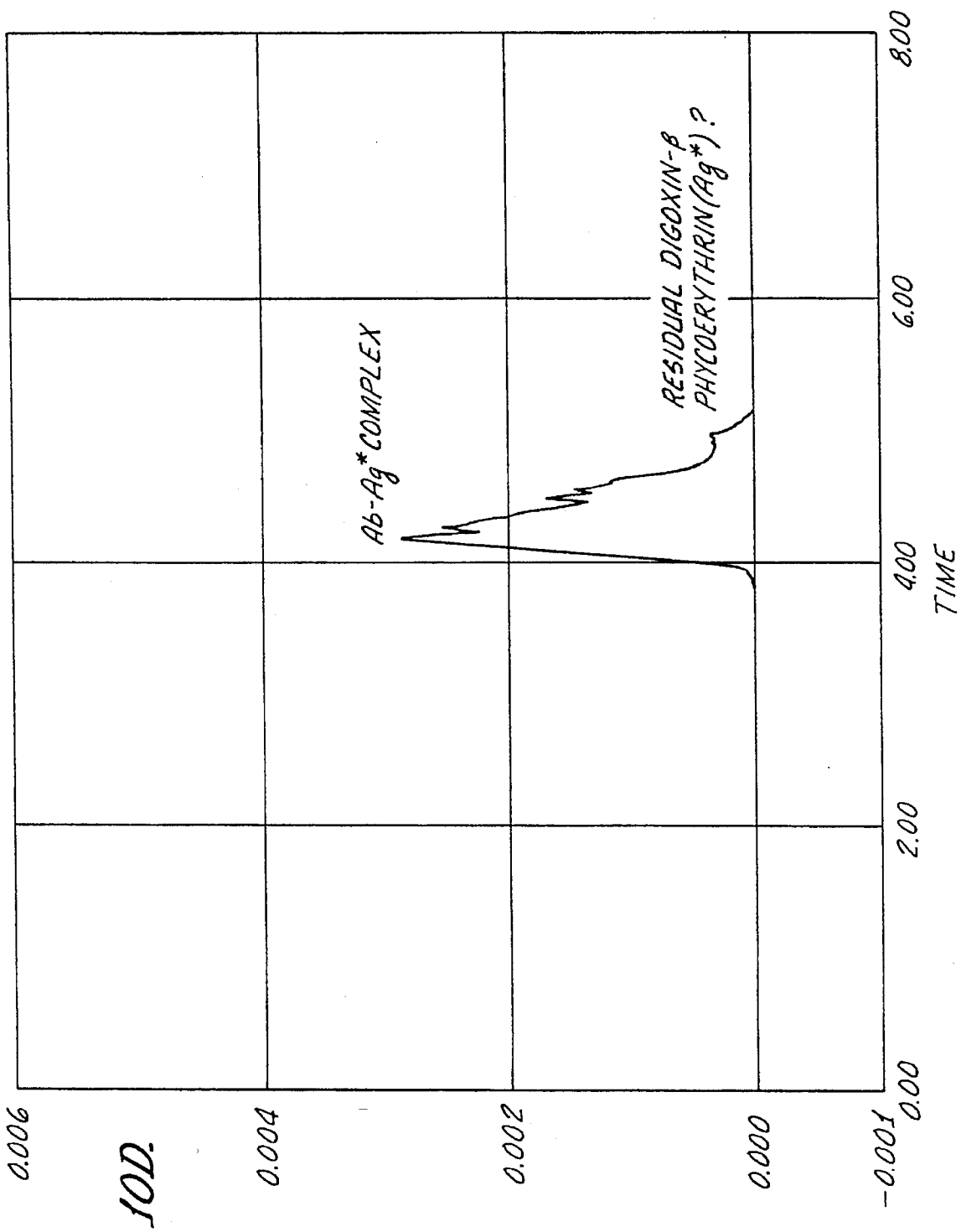

The presence of digoxigenin on each β-phycoerythrin of the synthesized digoxigenin-labeled β-phycoerythrin (D-BP*) is evident from FIG. 10D, in which excess antibody is added to D-BP* and the resulting mixture shows all D-BP* molecules are fully complexed with antibody in different ratios, as evidenced by the absence of the D-BP* peak in FIG. 10D. The broad heterogeneous peak with several shoulders was indicative of antibody-antigen complex at various molar ratios between Fab and the species with different numbers of digoxigenin molecules bound on β-phycoerythrin. More Fabs binding to a D-BP* results in a complex which migrates closer to the Fab molecule.

Analysis of D-BP* by CE-LIF at 2.5 to 25 ng/ml (equivalent to $10^{-11}$ to $10^{-10}$M) was demonstrated. At 2.5 ng/L of D-BP* (equivalent to $10^{-11}$M) signal attributable to D-BP* is approximately 10 times the baseline noise (data not shown), indicating the excellent lower limits of detection for this LIF system.

Figure 11A:
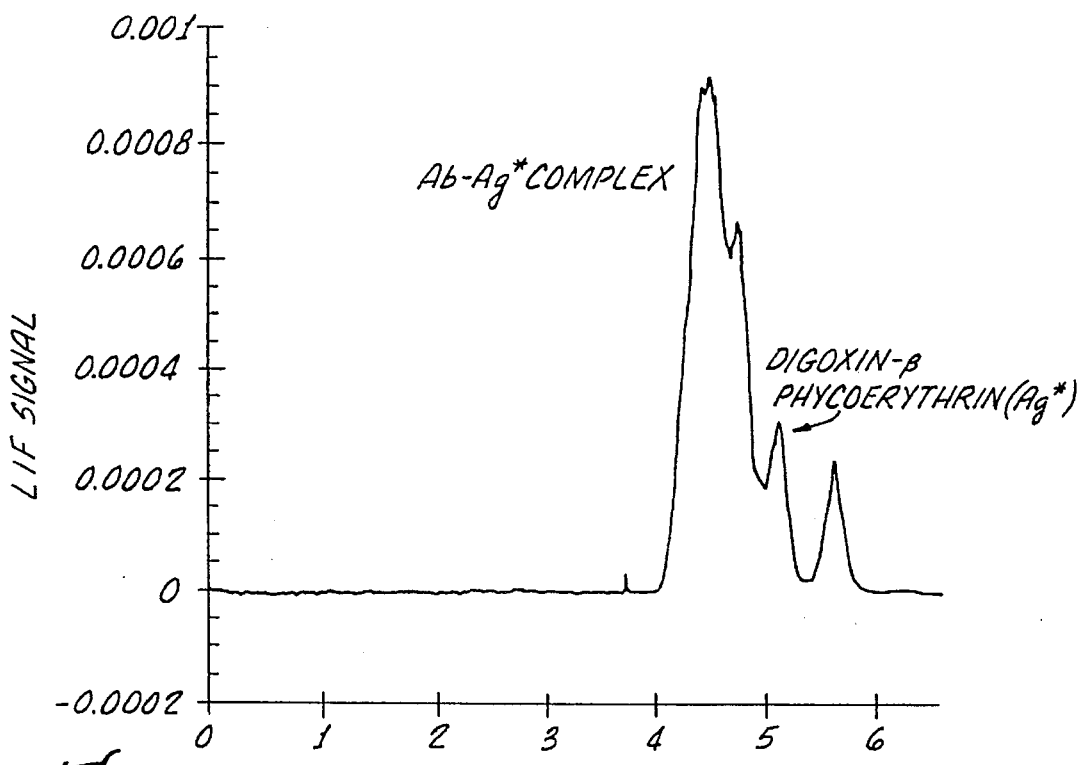
FIGS. 11A–11D demonstrate the calibration of digoxin using different concentrations of digoxin calibrators: 0.42 ng/ml (FIG. 11A); 2.72 ng/ml (FIG. 11B); 5.21 ng/ml (FIG. 11C), and 10.42 ng/ml (FIG. 11D).
Figure 11B:
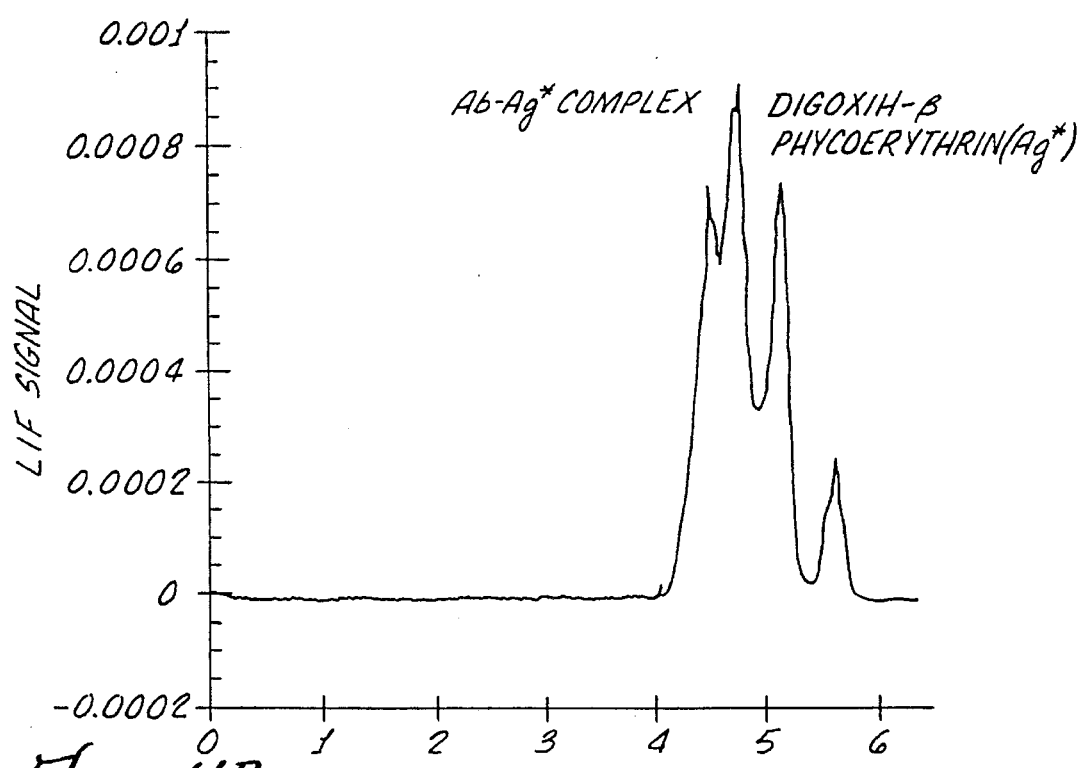
Figure 11C:
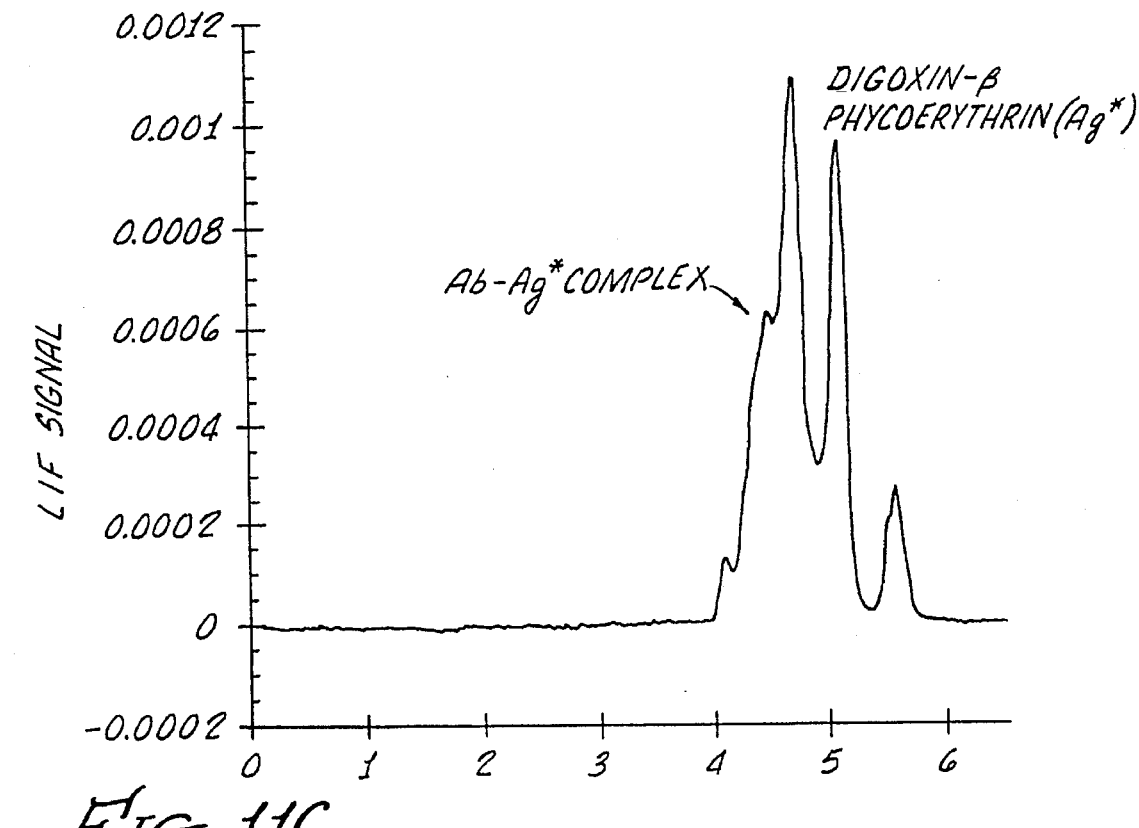
Figure 11D:
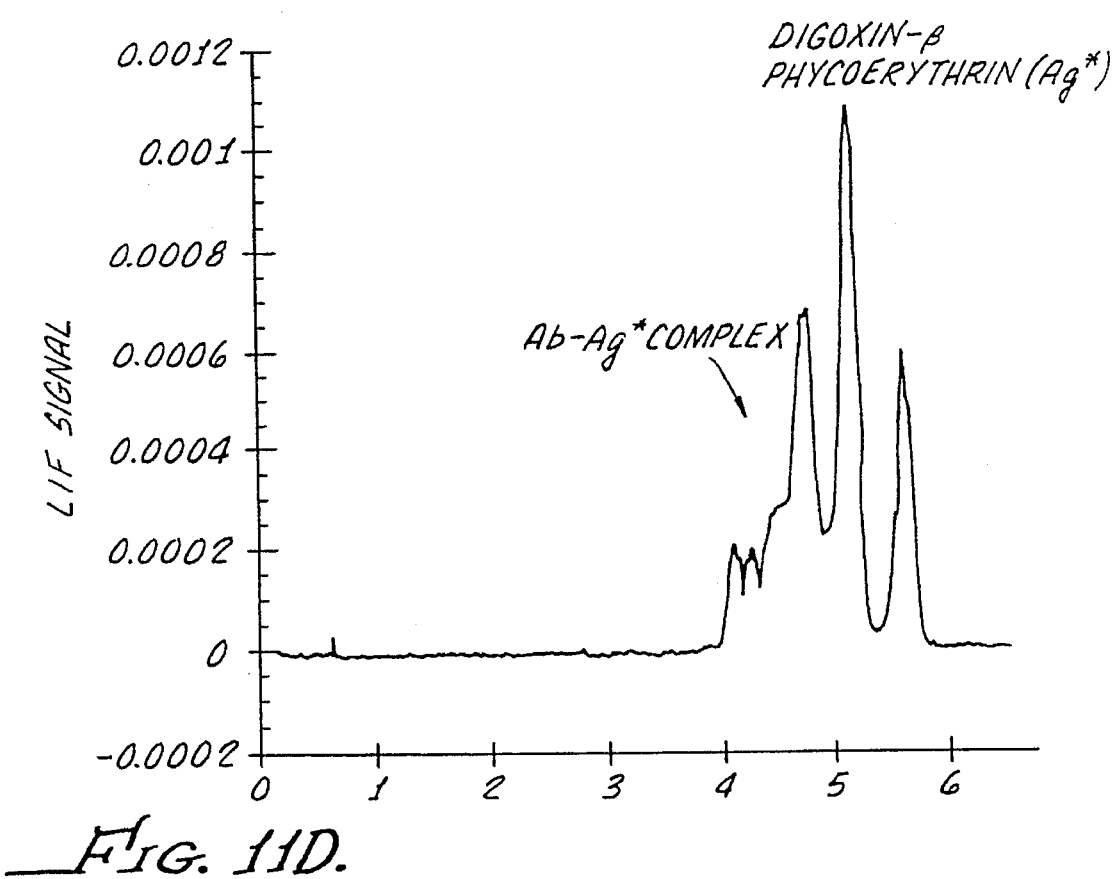
Figure 12:
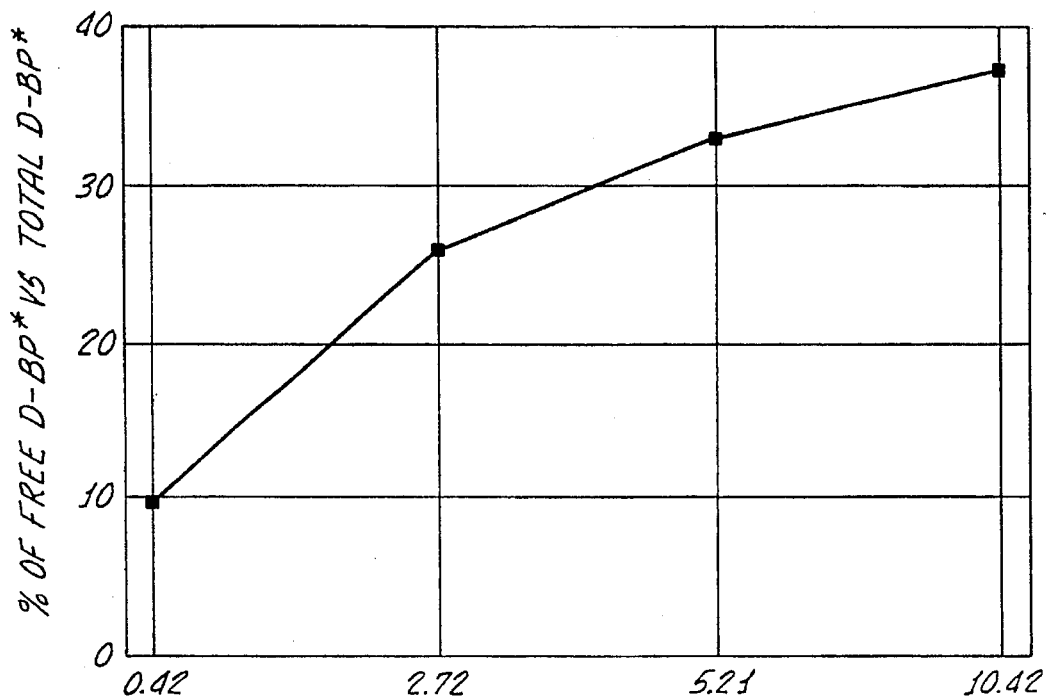
FIG. 12 is a digoxin calibration curve prepared from the ratio of the area between D-BP* and total area of Ab-D-BP*.
Figure 13:
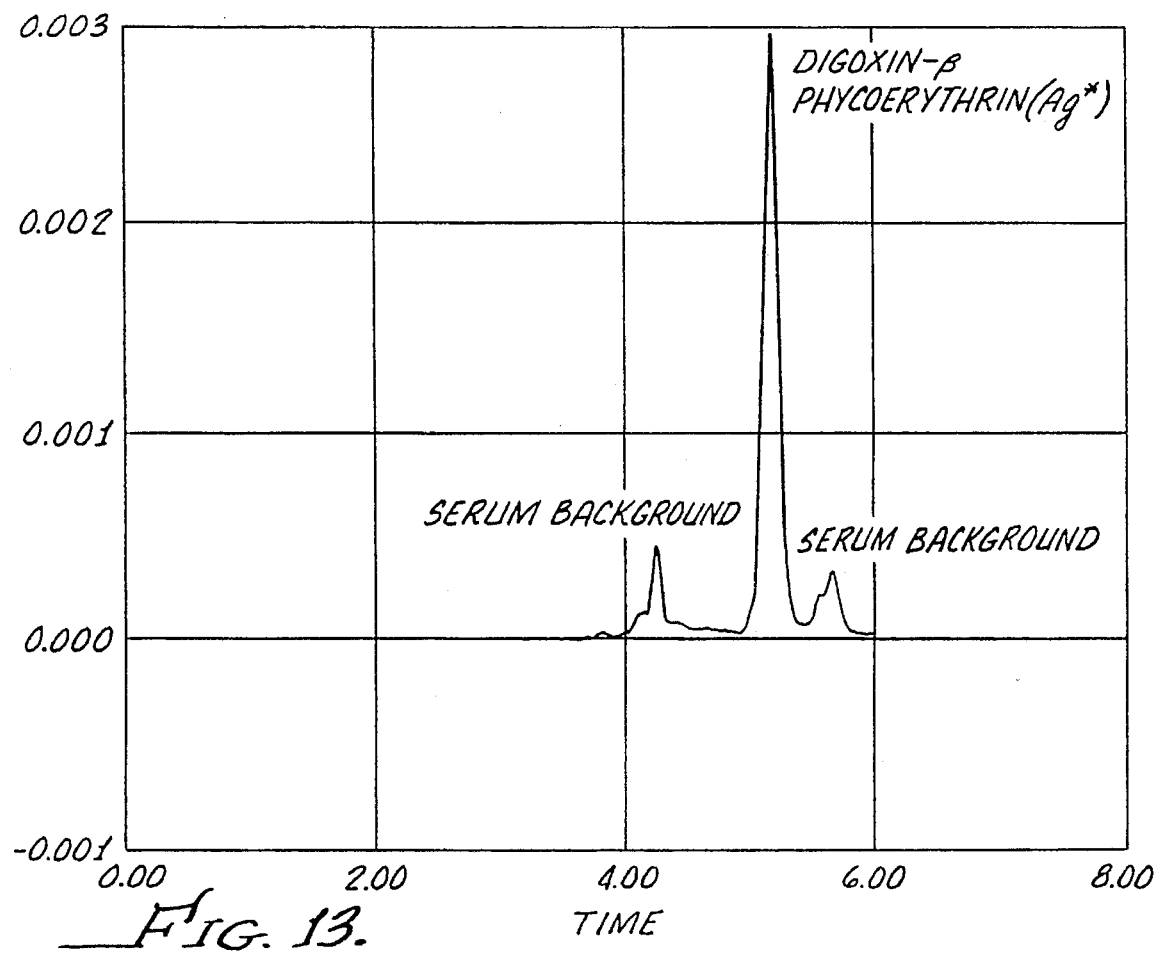
FIG. 13 shows the affect of serum on background levels in the CE/LIF assay.

The calibration of digoxin is demonstrated in FIGS. 11A through 11D which show calibrations using 50 μl of digoxin calibrators at concentrations of 0.42 ng/ml (FIG. 11A); 2.72 ng/ml (FIG. 11B); 5.21 ng/ml (FIG. 11C), and 10.42 ng/ml (FIG. 11D). As evidenced by the relative sizes of the peaks associated with the free labeled antigen (D-BP*) and the labeled antigen-antibody complex (Ab-Ag*) in this series of electropherograms, as the digoxin concentration in these samples is increased, competition between digoxin and labeled digoxin for antibody becomes readily apparent. As the digoxin concentration is increased in the sample the amount of free digoxin observed in the electropherogram also increases at the expense of the labeled antigen-antibody complex. This trend demonstrates the validity of the method of analysis. Using ratio of the area between D-BP* and total area of Ab-D-BP* (Ab-Ag*) and D-BP*, the digoxin calibration curve presented in FIG. 12 was produced. Reaction kinetics indicate that the immunoreaction reached its end point in 10 minutes according to the immunoreaction protocols. FIG. 13 shows that serum at 1 to 3 dilution does yield a relatively small fluorescent background under the LIF conditions employed.

In sum, the experiments demonstrate a CE/LIF based immunoassay technique that can be used to detect analytes at clinically useful concentration limits of analysis ($10^{-9}$ to $10^{-1}$M). In lieu of the β-phycoerythrin label, other fluorophores such as rhodamine or fluorescein derivatives attached to antigen with a well-defined charge which is independent of the pH of the running buffer may be employed. A positively charged species usually yields a sharper peak by CE under standard conditions, (electroosmotic flow toward the negative electrode), and is the most preferred competing species for the CE-LIF immunoassay.

EXAMPLE 4

IMPROVED CE/LIF DETECTION OF DIGOXIGENIN

Nielsen, R. G. et al. (*J. Chromatogr.* 539:177–185 (1991)) suggested that CE could be employed to study antibody-antigen reactions, and that if the antigen and antibody molecules were of comparable size, the peak due to the appreciably larger antibody-antigen complex could be clearly separated from those due to the free antibody and the free antigen. The measurements were made using UV absorbance, with the protein concentrations at about $4\times10^{-5}$M and in the absence of significant concentrations of potential interfering substances. Thus, such conditions did not provide assistance in evaluating typical clinical samples.

In accordance with the present invention and in order to extend CE such that it could be used to evaluate proteins and analytes present in a clinical sample, an alternative CE/LIF method was employed. For this alternate CE/LIF method, a P/ACE™ 2100 equipped with a laser induced fluorescence system by Beckman Instruments, Inc., Fullerton, Calif., was used with P/ACE system software controlled by an IBM PS/2 model 56 SX. The capillary column for CE/LIF was typically 27 cm length (20 cm to detector window)×75 μm i.d. (Polymicro Technologies, Phoenix, Ariz.) and was assembled in the P/ACE™ cartridge format with an ellipsoidal mirror to collect fluorescence. A 2.5 milliwatt green helium-neon laser emitting at 543.5 nm was purchased from Particle Measuring Systems, Boulder, Colo. A laser head-coupler to a standard SMA-905 fiber connector to the P/ACE system with LIFE detector was a product of OZ optics, Ontario, Canada. The fluorescence signal was collected through a narrow band filter of 590±9 nm (Oriel, Stratford, Conn.) while the laser beam was rejected by a notch filter at 543.5 nm (Barr Associates, Westford, Mass.).

Figure 14:
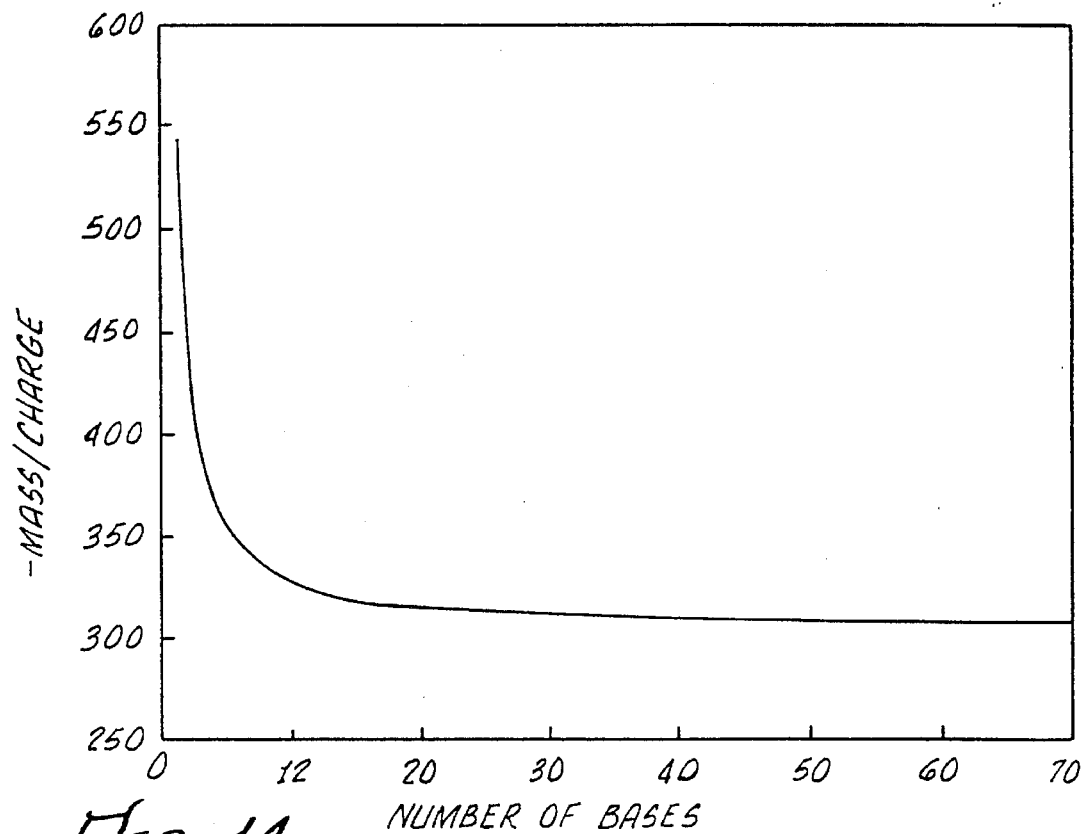
FIG. 14 shows the mass to charge ratio of the oligo-d(T) vs number of nucleotide bases.

In the alternate CE/LIF embodiment, the digoxigenin antigen was conjugated to an oligonucleotide. Such conjugation modulated the electrophoretic mobility of a labeled antigen. The mass-to-negative charge ratio of oligonucleotides decreases almost linearly with the oligonucleotide length, from 2 to 5 nucleotides, but rapidly reaches a plateau above 10 nucleotides. As the number of nucleotides increases, the mass-to-negative charge ratio reaches a plateau of −327 at approximately 10 nucleotides, and eventually reaches −306 with an infinite number of nucleotides at a buffer pH of 8.6, as shown in FIG. 14. Thus, the electrophoretic mobility of a synthetic oligonucleotide in an open capillary is approximately constant with the length of the oligo chain for a 10-mer or larger.

On the basis of above rationale, an oligonucleotide of $(dT)_{10}$ was selected as the charge modulator for an immunochemical study of digoxin as the antigen. Tetramethylrhodamine (TMR) was selected as the fluorescent label. The oligonucleotide was modified such that its 3' terminus contained a digoxigenin adduct, and its 5' terminus contained a tetramethylrhodamine label. The reagent was prepared from CPG-3'(FMOC-amino)-$(dT)_{10}$-5'amine in the following manner (CPG: control pore glass; FMOC: 9-Fluorennylmethoxycarbonyl). The synthesis of CPG-3'(FMOC-amino)-$(dT)_{10}$-5'amine was initiated with a 100 nmole CPG-3'-FMOC-amino column (Clontech, Palo Alto, Calif.). Synthesis was performed on a Pharmacia DNA synthesizer. The oligo $(dT)_{10}$ was capped at the 5'-end with an N-MMT-$C_6$-amino modifier (MMT: monomethoxytrityl), a CE phosphoramidite (Clontech, Palo Alto, Calif.). Deprotection of the N-MMT group with 50% acetic acid resulted in the formation of CPG-3'(FMOC-amino)-$(dT)_{10}$-5'amine.

Figure 16:
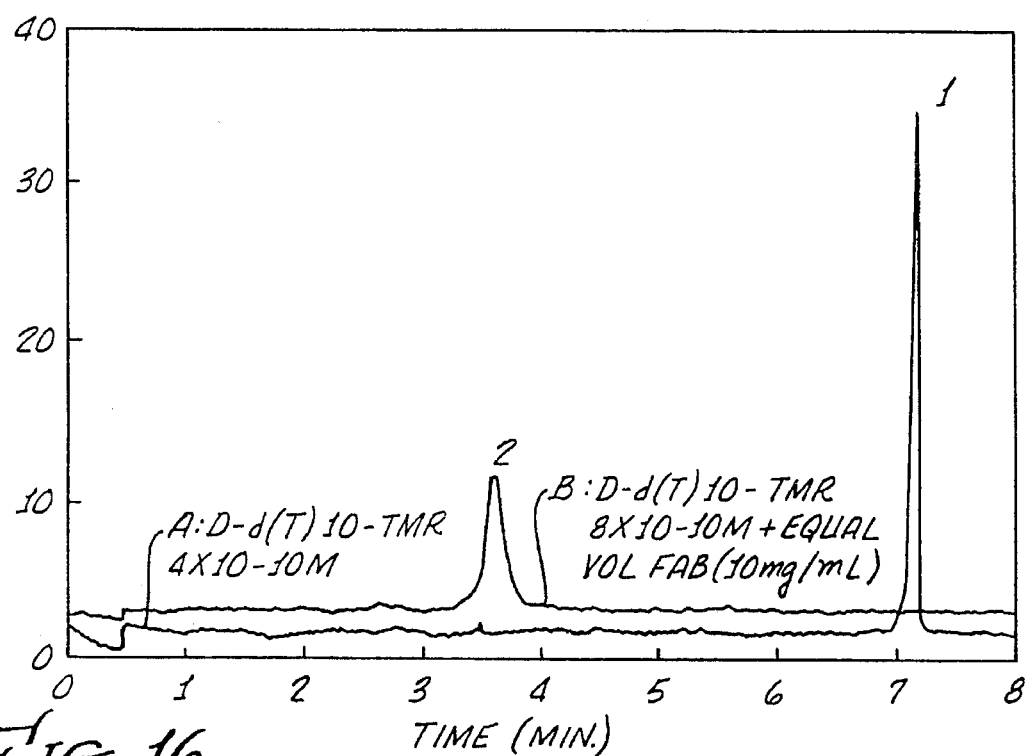
FIG. 16 shows electropherograms of digoxigenin-3'-d(T)$_{10}$-TMR at 4×10$^{-10}$M (A) and of the reaction product of Fab (50 μL, 10 μg/mL) to digoxin with digoxigenin-3'-d(T)$_{10}$-TMR (50 μL, 8×10$^{-10}$M) (B). Untreated fused-silica capillary, 75 μm (i.d.)×25 cm, were used; the applied potential was 7 kV/80 μA; Beckman protein analysis buffer was employed.

A portion of the CPG-3'(FMOC-amino)-$(dT)_{10}$-5'amine solid phase (50 nmole) was derivatized with 5-carboxytetramethylrhodamine succinimidyl ester (5 mg, Molecular Probes, Eugene, Oreg.) in acetonitrile (1.0 ml) at room temperature overnight. The resulting deep red colored solid phase was a tetramethylrhodamine (TMR) derivatized $d(T)_{10}$. Ammonia cleavage of the TMR-derivatized solid phase at room temperature for 2 hrs yielded a mixture that was fractionated on a reversed phase column (Beckman ODS Spherogel) to yield 3'-amino-$(dT)_{10}$-5'-TMR. Addition of digoxigenin-NHS ester (NHS: N-hydroxy succinimidylester; Boehringer Mannheim, Indianapolis, Ind.) to the 3'-amino-$(dT)_{10}$-5'-TMR, produced 3'digoxigenin-$(dT)_{10}$-5'-tetramethylrhodamine [3'-D-$(dT)_{10}$-5'-TMR] that was purified by gel-filtration chromatography (Sephadex G-25 column, 0.7 cm×15 cm) eluted with PBS. The procedure for the synthesis of 3'-digoxigenin-$(dT)_{10}$-5'-TMR is shown in FIG. 15. The purity of each of the intermediates was monitored by both HPLC and CE. The final product is homogeneous by CE/LIF, as shown in FIG. 16, tracing (A). The functional activity of the synthesized molecule was demonstrated in the digoxin immunoassay.

The immunoassay was conducted using an affinity purified Fab' fragment isolated from goat antiserum to digoxin (Boehringer Mannheim, Indianapolis, Ind.). Serum-based digoxin calibrators at 0.42, 2.782 and 5.21 ng/ml were obtained from Beckman Instruments Inc., Brea, Calif. Antibody was diluted in PBS containing 2 mg/ml BSA. A 50 μl aliquot of the 3'-D-$(dT)_{10}$-5'-TMR at $4×10^{-10}$M was mixed with 10 μl of serum calibrator and 20 μl of PBS containing 2 mg/ml BSA. Immunoreaction was initiated by the addition of 25 μl of the Fab' antibody (at 1.0 μg/ml) at room temperature for 10 minutes (end-point). Analysis of the immunoreaction products was performed on an automated capillary electrophoresis system equipped with a laser induced fluorescence detector (described above). Post-run data analysis was performed using System Gold™ software by Beckman Instruments Inc., Fullerton, Calif.

The addition of an excess of Fab' anti-digoxin to the modified antigen, 3'-digoxigenin-$(dT)_{10}$-5'-TMR (at $10^{-9}$M), resulted in the electropherogram shown in FIG. 16, tracing (B). A new broad peak occurred at 3.55 min, while the sharp peak for the 3'-digoxigenin-$(dT)_{10}$-5'-TMR species at 7.06 min in tracing (A) of FIG. 12 disappeared completely. The occurrence of the new, broader peak at 3.55 min at the expense of the peak at 7.06 min indicated the formation of a 1:1 complex between the Fab' and the 3'-digoxigenin-$(dT)_{10}$-5'-TMR. The broad peak observed for the antibody complex with 3'-digoxigenin-$(dT)_{10}$-5'-TMR represents essentially the image of the electrophoretic mobility of the Fab' molecule. The Fab' antibody-bound and the free 3'-digoxigenin-$(dT)_{10}$-5'-TMR species are clearly well-separated and well-suited for digoxin immunoassay.

Figure 17:
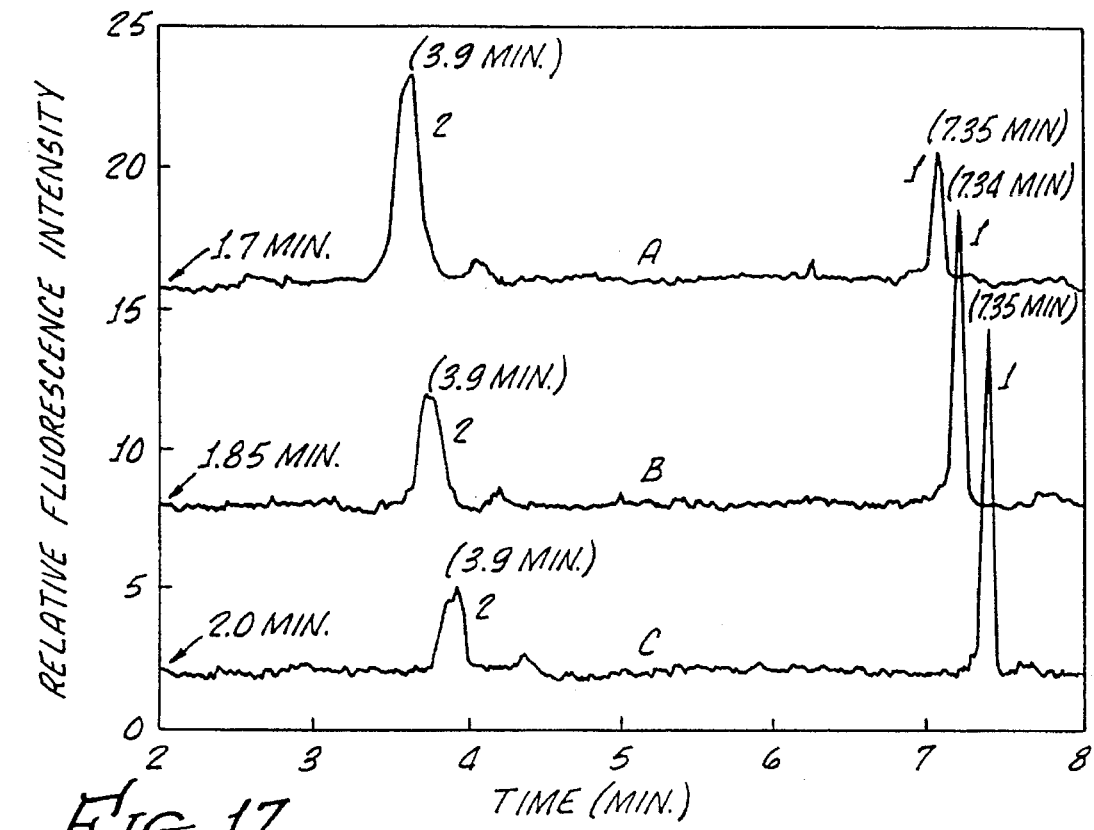
FIG. 17 shows electropherograms of a digoxin assay mixture with serum calibrator at 0.42 (A), 2.72 (B) and 5.21 ng/ml (C). The conditions used are the same as in FIG. 16. Peaks: 1=digoxigenin-3'-d(T)$_{10}$-TMR; 2=Antigen-antibody complex of the Fab.

The use of serum-based digoxin calibrators in the digoxin immunoassay is demonstrated in FIG. 17 for digoxin concentrations of 0.42 ng/ml (tracing (A)), 2.72 ng/ml (tracing (B)) and 5.13 (tracing (C)) ng/ml. As the digoxin concentration was increased in the sample, the peak for the free 3'-digoxigenin-$(dT)_{10}$-5'-TMR also increased. Meanwhile, the peak observed for the antigen-antibody complex was found to decrease. This trend demonstrated the validity of the CE/LIF method of analysis. The competitive immunoassay can be represented by the following equilibrium expression:

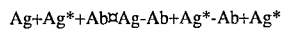

$$Ag+Ag^*+Ab \rightleftharpoons Ag\text{-}Ab+Ag^*\text{-}Ab+Ag^*$$

Figure 18:
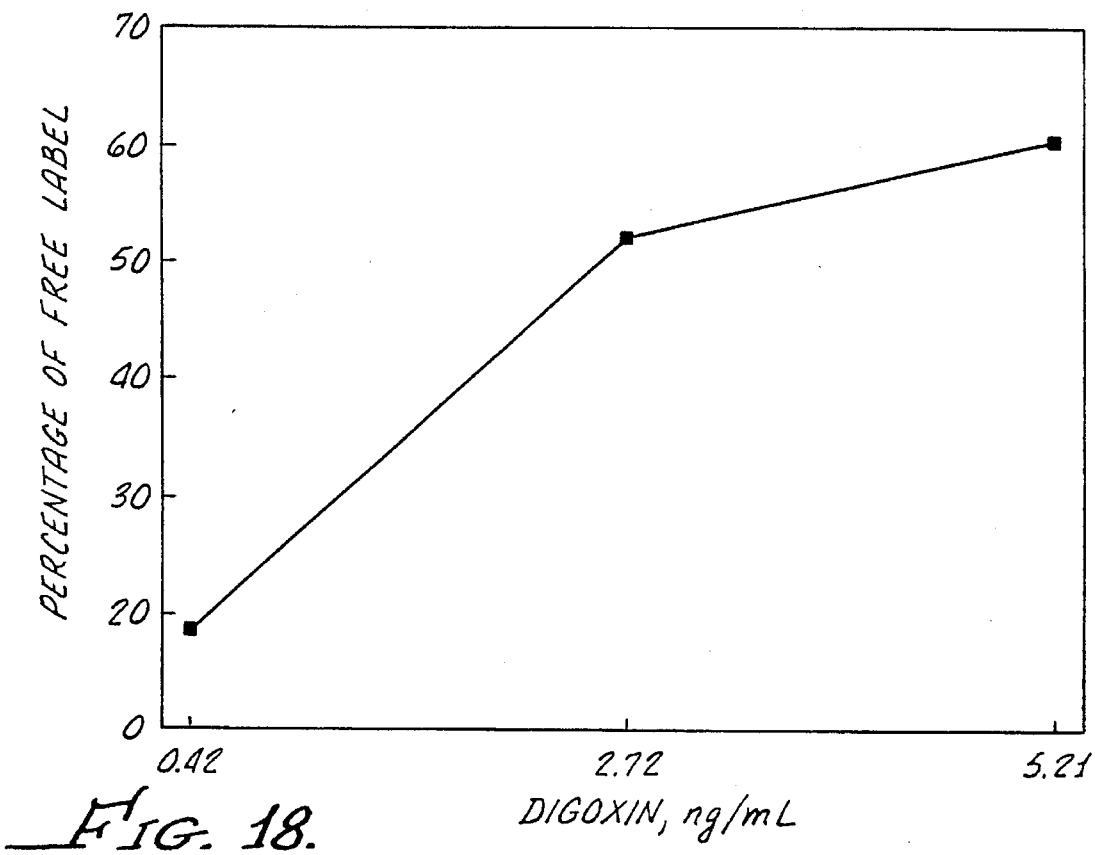
FIG. 18 shows a calibration curve for digoxin assay by CE-LIF. The data is presented as percentage of free digoxigenin-3'-d(T)$_{10}$-TMR vs digoxin calibrators.

The digoxin calibration curve (FIG. 18) was produced by using the area ratio of the fluorescence signal of the peak for free 3'-digoxigenin-$(dT)_{10}$-5'-TMR (Ag*) to the total fluorescence signal in each electropherogram. The amounts of both bound and free 3'-digoxigenin-$(dT)_{10}$-5'-TMR can be obtained simultaneously. The observed reaction kinetics indicate that the immunoassay reaches equilibrium within 10 minutes (Freytag, J. W. et al., *Clin. Chem.* 30:417–420 (1984)) under the immunoreaction conditions.

The above results demonstrate the utility of CE/LIF for immunoassay. The modulation of the electrophoretic mobility of a labeled antigen, a competing species for the specific antibody, has been shown for a competitive immunoassay (Rubenstein, K. E. et al., *Biochem. Biophys. Res. Commun.* 47:846–850 (1972); Jolley, M. E. et al., *Clin. Chem.* 27:1190–1197 (1981). The use of an oligonucleotide provides an example of the charge-based modification of a labeled hapten for immunoassay.

For a large molecule such as a protein antigen, a monoclonal antibody to an epitope of the protein antigen is preferred. The epitope is usually a synthetic peptide of 5 to 10 amino acids that may be used as the competing species for immunoassay. For the direct assay of a protein antigen, modulation of the electrophoretic mobility of an antibody can be accomplished, preferably using a monoclonal antibody for the protein antigen. The antibody-antigen complex is expected to have a charge-to-mass ratio at the arithmetic mean of those of the antigen and the modified antibody. Thus, if the antibody is fluorophore-labeled and used in excess with respect to the protein antigen, the amount of the complex formed should be directly proportional to the concentration of the protein antigen Thus, only a single antibody species, rather than the pair of antibody species required for sandwich immunoassays (Schuurs, A. H. W. M. et al., *Clin. Chem. Acta.* 81:1–8 (1977)) with solid phase separation, is required for immunoassay using the CE/LIF technique. The use of excess antibody in solution should provide more favorable reaction kinetics than found with the traditional solid phase-based sandwich immunoassay.

The combination of charge modulation of the antibody or antigen and powerful capillary electrophoresis separation, along with laser induced fluorescence detection, promises to be a powerful tool for many other immunoassays for clinical diagnostic applications.

EXAMPLE 5

CE/LIF DETECTION IN ENZYMATIC ANALYSIS

A CE/LIF method of the present invention was used to study the kinetics of protease catalyzed hydrolysis of a cyanine dye labeled angiotensin I protein (asp-arg-val-tyr-Ile-his-pro-phe-his-leu). Angiotensin I was labeled with Cy3, a cyanine dye having a 532 nm excitation and a 580 nm emission, and then digested with protease. The products of the digestion reaction which are known to include angiotensin II (asp-arg-val-tyr-Ile-his-pro-phe) were analyzed using CE/LIF techniques.

More particularly, Cy3, a carboxyl activated cyanine dye (from Biological Detection Systems, Pittsburgh, Pa.) having the following structure:

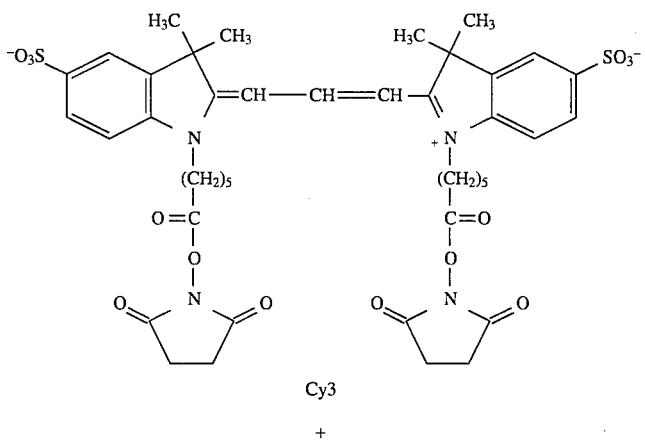

Cy3

+ was used to label angiotensin I, angiotensin II (frown Sigma Chemical, St. Louis, Mo.) and aspartic acid according. The labeling method resulted an N-α-terminal aspartic acid residue of each protein having a bound Cy3 label.

To prepare the labelled proteins and aspartic acid, separate solutions of angiotensin I, angiotensin II, and aspartic acid were prepared to a concentration of 1.0 mg/mL in 50 mM phosphate buffer at a pH of 7.5. Then 46 moles of each solution was added to three different containers containing 80 nmole of Cy3 and allowed to react at room temperature for 1 hr. The reaction products for each reaction were chromatographed on a $C_{18}$ reverse-phase column using an eluting solution of methanol and 20 mM phosphate buffer at pH 6.0 on a Beckman System Gold LC equipped with a diode array detector. Purity was continued using LC, CE and UV/Visible spectrophotometry.

The CE/LIF system was a P/ACE 2100 equipped with a laser induced fluorescence system available from Beckman Instruments, Inc. of Fullerton, Calif. The system was controlled with P/ACE system software on an IBM PS/2 model 55 SX. Post run data analysis was performed on System Gold software supplied on the P/ACE system. The capillary columns were 27 cm overall length (20 cm to detector window) with a 20 μm diameter purchased from Polymicro Technologies in Phoenix, Ariz. The capillary columns were assembled in the P/ACE cartridge format with an ellipsoidal mirror to collect fluorescence. A 15 milliwatt frequency-doubled diode laser emitting a 532 nm was provided by Amoco Laser, Naperville, Ill. and the laser headcoupled to a standard SMA-906 fiber connector to the P/ACE system with the LIF detector was a product of OZ optics, Ontario, Canada. The fluorescence signal was collected through a narrow bank filter of 590 nm±9 nm provided by Oriel, Stratford, Conn. and the laser beam was rejected by a 532 nm notch filter supplied by Applied Physics, Torrance, Conn. A 5 milliwatt green helium-neon laser (543 nm) was purchased from Particle Measurement System of Denver, Colo.

Figure 19:
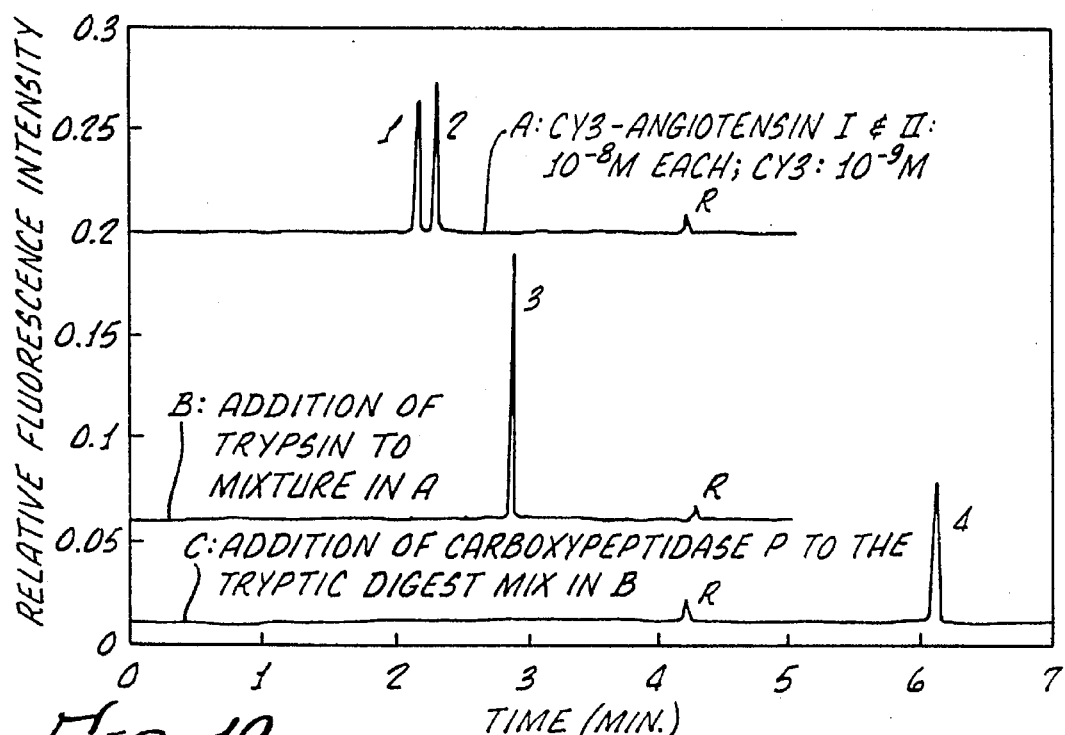
FIG. 19 shows electropherograms of fluoro labeled angiotensin and angiotensin digestion mixtures. Electropherogram (A) is that of labeled angiotensin I & II and the fluoro label. Electropherogram (B) is that of a trypsin digestion mixture of the mixture shown in (A). Electropherogram (C)

Prior to performing an angiotensin I digestion by proteinase. K, control digestion experiments and control electropherograms were obtained on the described P/ACE system using low pressure injection (0.5 psi) for 20 seconds and allowing the sample constituents to migrate under in a 200 mM borate buffer at pH 10.2 under a voltage gradient of 740 V/cm (20 kV, 30 μA) at room temperature. FIG. 19, electropherogram A, shows the relative migration times of $10^{-8}$M control samples of Cy3-angiotensin I and II, respectively, with the peaks showing migration times at 2.1 minutes and 2.24 minutes, respectively. The peak at 4.2 minutes migration time is Cy3 diacid at a concentration of $10^{-9}$M. When the enzyme trypsin is added to the solution used to obtain electropherogram A, the electropherogram shown at FIG. 19 (B) results with a single peptide fragment appearing at 2.8 minutes. The specificity of the trypsin digestion on Cy3-angiotensin I and Cy3-angiotensin II (a product of angiotensin I proteinase K digestion) suggests that this single peptide fragment may be Cy3-asp-arg. When carboxypeptidase P is added to the mixture containing the trypsin digestion, to the formation of Cy3-aspartic acid occurs, as shown in FIG. 19(C).

To perform proteinase K digestion of Cy3-angiotensin I, 90 μL of a $10^{-8}$M solution of Cy3-angiotensin I (in 0.05M Tris-HCl buffer at pH 8.0) was incubated at room temperature with 10 μL proteinase K having a solution activity of 0.1 U/mL. The reaction was sampled during the digestion and the sample constituents analyzed as described above by CE/LIF.

A pre-reaction electropherogram of the reference marker, the Cy3-diacid, and Cy3-angiotensin I was obtained (See FIG. 20 electropherogram A). Immediately after the addition of proteinase K to the reaction mixture, at 0.1 minute reaction time, about 30% Cy3-angiotensin I was hydrolyzed to Cy3-angiotensin II as indicated in electropherogram (B) of FIG. 20. As shown in FIG. 20, electropherogram (C), eight minutes after the addition of proteinase K, nearly all Cy3-angiotensin I was converted to Cy3-angiotensin II, the peak at 2.25 minutes migration time. A minor product X, migration time, 2.8 minutes also begins to form. After 24 minutes reaction time, compound X becomes a major product at the expense of Cy3-angiotensin II and a second minor component Y forms. This is demonstrated in the electropherogram of FIG. 21, electropherogram (D) with Y appearing at 2.6 minutes.

Following continued digestion as shown in FIG. 21 electropherograms E and F, compound Y increases and Z forms. Z's electrophoretic migration is shown just after that of X. Finally, after continued and exhaustive digestion, compound Z increases and eventually is the only end product. (See FIG. 22 electropherograms G and H.) This end product is identical to that of the product of tryptic digestion of Cy3-angiotensin I and II shown in FIG. 19 electropherogram (B). When compound Z, the end product of exhaustive digestion of the Cy3-angiotensin protein, is digested in the presence of carboxypeptidase P Cy3-aspartic acid is the resulting product. This is substantiated by FIG. 19 electropherogram C.

The above described experiment demonstrates the usefulness of LIF-CE based enzyme assays using a fluoro labeled substrate. Since the labeled substrate is stable, it is well suited for low level enzyme contaminant assays and can be extended to restriction enzyme activity or DNA hybridization probe assays where the labeled substrate or probe can be separated from the product by CE and monitored with LIF. The methods of the present invention are particularly suit for analyzing enzymes in situation where prior art sample matrices are a potential interference. In accordance with the present invention, fluoro labeled peptides are used as a stable substrate for to interrogate the activity and specificity of an enzyme. Enzyme activity on the labeled substrate would result in shortening of the labeled peptide to at least one product that can be readily separated and identified by CE/LIF. Furthermore, using a fluorescently labeled peptide substrate, enzymes in a complex mixture can be analyzed with minimum interference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of assaying the concentration of an analyte in a sample which comprises:
   (A) incubating said sample in the presence of a fluorophore labelled analyte comprising said analyte attached to at least one nucleotidyl residue which contains a fluorescent moiety and an immunoglobulin which specifically binds to said analyte and to said fluorophore labelled analyte, wherein said incubation is conducted under conditions sufficient to permit formation of an immunoglobulin-analyte complex and/or an immunoglobulin-fluorophore labelled analyte complex;
   (B) subjecting an amount of said incubated sample of step (A) to capillary electrophoresis, wherein said capillary electrophoresis is conducted under conditions sufficient to separate said fluorophore labeled analyte from said immunoglobulin-fluorophore labelled analyte complex; and
   (C) assaying said concentration of analyte by detection of a laser induced fluorescence of said fluorophore, wherein said laser induced fluorescence is inversely proportional to the concentration of said analyte in said sample.

2. The method of claim 1, wherein said analyte is a protein, and said sample is selected from the group consisting of blood, serum, cerebrospinal fluid, urine and milk.

3. The method of claim 2 wherein in step (A), said protein is an enzyme, receptor, immunoglobulin or toxin.

4. The method of claim 1, wherein said analyte is a non-proteinaceous organic molecule, and said sample is selected from the group consisting of water, soil, and foodstuff.

5. The method of claim 1, wherein in step (A), said immunoglobulin is selected from the group consisting of a polyclonal antibody, a monoclonal antibody, an Fab fragment, an F(ab)$_2$ fragment and a single-chain immunoglobulin.

6. The method of claim 1, wherein in step (A), said fluorescent moiety is selected from the group consisting of fluorescein, isothiocyanate, rhodamine, phycoerythrin, phycocyanin, allophycocyanin, o-phthaldehyde label, fluorescamine, and tetramethylrhodamine.

7. The method of claim 6, wherein said fluorescent moiety is tetramethylrhodamine.

8. The method of claim 1, wherein said fluorophore labelled analyte comprises said analyte attached to a BODIPY labelled oligonucleotide.

9. The method of claim 8, wherein said oligonucleotide contains ten nucleotidyl residues.

10. The method of claim 1, wherein said fluorophore labelled analyte has the formula:

$$A\text{-}3'\text{-}[N]_x\text{-}5'\text{-}F$$

wherein A is the analyte being assayed, N is a nucleotide residue, x is the number of nucleotidyl residues with a value between 1 and 20, and F is a fluorescent moiety.

11. The method of claim 10, wherein x=10, and wherein F is tetramethylrhodamine.

12. The method of claim 1, wherein in step (B), said capillary electrophoresis is conducted in an uncoated, fused silica column.

* * * * *